US010442862B2

(12) United States Patent
Yang et al.

(10) Patent No.: US 10,442,862 B2
(45) Date of Patent: Oct. 15, 2019

(54) USE OF EGFR BIOMARKERS FOR THE TREATMENT OF GASTRIC CANCER WITH ANTI-EGFR AGENTS

(71) Applicant: CROWN BIOSCIENCE, INC. (TAICANG), Jiangsu Province (CN)

(72) Inventors: Jie Yang, Changping (CN); Yiyou Chen, San Jose, CA (US); Henry Qixiang Li, Carlsbad, CA (US); Jie Cai, Changping (CN)

(73) Assignee: Crown Bioscience, Inc. (Taicang), Jiangsu Province (CN)

( * ) Notice: Subject to any disclaimer, the term of this patent is extended or adjusted under 35 U.S.C. 154(b) by 209 days.

(21) Appl. No.: 14/775,117

(22) PCT Filed: Mar. 14, 2014

(86) PCT No.: PCT/US2014/028714
§ 371 (c)(1),
(2) Date: Sep. 11, 2015

(87) PCT Pub. No.: WO2014/153018
PCT Pub. Date: Sep. 25, 2014

(65) Prior Publication Data
US 2016/0024216 A1    Jan. 28, 2016

(30) Foreign Application Priority Data
Mar. 14, 2013 (WO) ................ PCT/CN2013/072638

(51) Int. Cl.
C07K 16/28    (2006.01)
A61K 31/7068    (2006.01)
A61K 33/24    (2019.01)
A61K 39/395    (2006.01)
A61K 45/06    (2006.01)
C12Q 1/6886    (2018.01)
G01N 33/574    (2006.01)
A61K 39/00    (2006.01)

(52) U.S. Cl.
CPC ...... *C07K 16/2863* (2013.01); *A61K 31/7068* (2013.01); *A61K 33/24* (2013.01); *A61K 39/39558* (2013.01); *A61K 45/06* (2013.01); *C12Q 1/6886* (2013.01); *G01N 33/57446* (2013.01); *A61K 2039/505* (2013.01); *C07K 2317/24* (2013.01); *C07K 2317/76* (2013.01); *C12Q 2600/106* (2013.01); *C12Q 2600/158* (2013.01); *G01N 2333/71* (2013.01)

(58) Field of Classification Search
None
See application file for complete search history.

(56) References Cited

U.S. PATENT DOCUMENTS

| 2008/0090233 A1 | 4/2008 | Garcia et al. |
| 2009/0017050 A1 | 1/2009 | Powell et al. |
| 2009/0214541 A1 | 8/2009 | Gillies et al. |
| 2011/0230360 A1* | 9/2011 | Stephan ............... C12Q 1/6886 506/7 |

FOREIGN PATENT DOCUMENTS

| JP | 2008-502328 A | 1/2008 |
| WO | WO 2005/117553 A2 | 12/2005 |
| WO | WO 2012/157647 A1 | 11/2012 |
| WO | WO 2014/139131 A1 | 9/2014 |
| WO | WO 2014/153018 A1 | 9/2014 |

OTHER PUBLICATIONS

Nicholson et al (EJC, 37:S9-S15, 2001).*
Kim et al (52:738-746, 2008).*
Luber et al (BMCC, 11:509, pp. 1-10, 2011).*
Moehler et al (AO, 22:1358-1366, 2011).*
English translation of the Search Report in related Chinese Patent Application No. 201480026267.6, dated Sep. 26, 2016.
Liu et al., "Clinical significance of EGFR expression in Chinese gastric cancer patients", *World Chinese Journal of Digestology*, 18(25):2648-2653, 2010.
Dragovich et al., "Anti-EGFR-Targeted Therapy for Esophageal and Gastric Cancers: An Evolving Concept", *Journal of Oncology*, vol. 2009, Article ID 804108, pp. 1-8, 2009.
English translation of the Examination Report in related Chinese Patent Application No. 201480026267.6, dated Jun. 14, 2017.
Hara et al. "Interleukin-2 protentiation of cetuximab antitumor activity for epidermal growth factor receptor-overexpressing gastric cancer xegnografts through antibody-dependent cellular cytotoxicity", Cancer Sci. Jul. 2008, 99(7):1471-1478.
Dragovich et al. "Anti-EGFR-Targeted Therapy for Esophageal and Gastric Cancers: An Evolving Concept" Journal of Oncology. pp. 1-8 Jul. 2009.
Hirsch et al. "Predictive value of EGFR and HER2 overexpression in advanced non-small-cell lung cancer" Oncology. 28:S32-S37.
Zhang et al. "A subset of gastric cancers with EGFR amplification and overexpression respond to cetuximab therapy" Nature. Scientific Report 3. Article No. 2992, pp. 1-6 Oct. 2013.
International Search Report based on International Patent Application PCT/US2014/028714, dated Jul. 15, 2014.
Written Opinion based on International Patent Application PCT/US2014/028714, dated Jul. 15, 2014.
International Preliminary Report on Patentability for International Patent Application No. PCT/CN2013/072638, dated Sep. 15, 2015, 6 pages.
International Preliminary Report on Patentability for International Patent Application No. PCT/US2014/028714, dated Sep. 15, 2015, 10 pages.

(Continued)

*Primary Examiner* — Brad Duffy
(74) *Attorney, Agent, or Firm* — Cooley LLP

(57) ABSTRACT

The present invention relates to methods for treating gastric neoplasias, in particular treating patients who have been previously determined to have an EGFR biomarker. Gastric carcinoma (GC) is one of the most common and deadliest cancers with ~1 million diagnoses and ~0.7 million deaths each year worldwide, with high incidence in Eastern Asia.

8 Claims, 12 Drawing Sheets

Specification includes a Sequence Listing.

(56) References Cited

OTHER PUBLICATIONS

International Search Report and Written Opinion for International Patent Application No. PCT/CN2013/072638, dated Dec. 19, 2013, 10 pages.
Office Action and English translation, dated Nov. 1, 2017, for corresponding Japanese Application No. 2016-502876, 8 pages.
Pinto, et al., "Phase II study of cetuximab in combination with cisplatin and docetaxel in patients with untreated advanced gastric or gastro-oesophageal junction adenocarcinoma (DOCETUX study)." British Journal of Cancer (2009); 101: 1261-1268.
Zhao, Ya-juan et al., "Expression of EGFR and its clinical significance in gastric adenocarcinoma tissues." Chin J Cancer Prev Treat (2010); 17(4): 273-274 (with English Abstract).
English translation of the Examination Report in corresponding Japanese Patent Application No. 2016-502876, dated Aug. 27, 2018, 8 pages.
Furuta, et al., "S15-1. Genome Biomarker of Molecular Targetting Therapy for Gastrointestinal Disorders." Jpn. J. Clin. Pharmacol. Ther. (2011); 42 (3):165-166. [Non-English].
Kimura, et al., "Antibody-dependent cellular cytotoxicity of cetuximab against tumor cells with wild-type or mutant epidermal growth factor receptor." Cancer Science (2007); 98 (8): 1275-1280.
Yokoyama, et al., "Molecular basis for sensitivity and acquired resistance to gefitinib in HER2-overexpressing human gastric cancer cell lines derived from liver metastasis." British Journal of Cancer (2006); 95 (11): 1504-1513.
Yokozaki, H., "Molecular characteristics of eight gastric cancer cell lines established in Japan." Pathology International (2000); 50 (10): 767-777.
Liang, Z., et al., "Analysis of EGFR, HER2, and TOP2A gene status and chromosomal polysomy in gastric adenocarcinoma from Chinese patients." BMC Cancer (2008); 8: 363, pp. 1-12.

* cited by examiner

USE OF EGFR BIOMARKERS FOR THE TREATMENT OF GASTRIC CANCER WITH ANTI-EGFR AGENTS

CROSS-REFERENCE TO RELATED APPLICATIONS

This application is the national stage of International Patent Application No. PCT/US2014/20714, filed Mar. 14, 2014, which claims priority to, and the benefit of International Patent Application No. PCT/CN2013/072638, filed on Mar. 14, 2013, each of which is herein incorporated by reference in its entirety for all purposes.

FIELD OF THE INVENTION

The present invention relates generally to methods for treating gastric neoplasias, in particular treating patients who have been previously determined to have a specific epidermal growth factor receptor (EGFR) biomarker.

BACKGROUND OF THE INVENTION

Gastric carcinoma (GC) is one of the most common and deadest cancers with ~1 million diagnoses and ~0.7 million deaths each year worldwide[1], with high incidence in Eastern Asia[2]. However, very few effective treatment options are available beyond surgery for the majority of GC patients. Trastuzumab (Herceptin®), a monoclonal antibody targeting HER2, is the only approved target therapy, but is limited to a small fraction of GC patients with higher HER2 (EGFR2) gene expression[3] and amplification. The recently approved drugs that can demonstrate significant benefits in GC could be particularly attractive to meet such an urgent need. EGFR, also referred to as ERBB1/HER1, belongs to the same family of HER2 and is a receptor tyrosine kinase (RTK) expressed in epithelia cancers, including colorectal carcinoma (CRC), GC and non-small cell lung carcinoma (NSCLC), etc. Cetuximab is a monoclonal antibody, that binds to EGFR and blocks its ligand induced downstream signaling, thus inhibiting cell proliferation. Cetuximab was approved by Food and Drug Administration (FDA) for treating EGFR-expressing metastatic CRC (mCRC) without activating KRAS mutations at codons 12/13[4], and squamous cell carcinoma of head and neck (SCCHN)[5], but Cetuximab has yet to be approved for treatment for GC. There are several phase II clinical trials on the combination treatments of cetuximab/chemotherapy agents for advanced GC but the studies have yet to demonstrate significant superior clinical benefit over the current standard of care (SOC)[6-8]. A randomized controlled phase III trial sponsored by Merck Serona has been recently reported to fail to meet its primary endpoint (NCT00678535: Erbitux in Combination With Xeloda and Cisplatin in Advanced Esophago-gastric Cancer, or EXPAND).

New effective target therapy is therefore urgently needed. The present invention provides this and other advantages.

SUMMARY OF THE INVENTION

One aspect of the present invention provides a method for treating gastric neoplasia comprising administering to a patient in need of such treatment an effective amount of a drug. In some embodiments, the drug is against epidermal growth factor receptor (EGFR). In some embodiments, the drug is against the signaling pathway downstream of EGFR. In some embodiments, the drug is an antagonist or an antibody of the ligand of EGFR, for example, an antagonist or an antibody of epidermal growth factor (EGF), transforming growth factor α (TGFα), HB-EGF, amphiregulin, betacellulin, epigen, and/or epiregulin. In some embodiments, the drug is a small molecule. In some embodiments, the drug is against a heterodimer formed by EGFR and another member of the ErbB receptor family such as ErbB2/Her2/neu. In some embodiments, the drug is against a homodimer formed by EGFRs. In some embodiments, the drug is an antibody or antibody like therapeutic entity against EGFR (anti-EGFR antibody treatment), e.g., cetuximab. In some embodiments, the patient has been determined to contain an EGFR biomarker. In one embodiment of the method the gastric neoplasia is gastric adenocarcinoma. In another embodiment of the method the anti-EGFR agent is an anti-EGFR antibody. In another embodiment, the anti-EGFR agent is cetuximab, panitumumab, nimotuzumab, antibody 806, Sym004, or MM-151. In certain embodiments, the anti-EGFR agent is a combination of 2 or more anti-EGFR agents. In another embodiment, the method further comprises administering the anti-EGFR agent in combination with the standard treatment for gastric neoplasia. In one embodiment, the method further comprises administering the anti-EGFR agent in combination with chemotherapy or radiation therapy. In yet a further embodiment, the method comprises administering the anti-EGFR agent in combination with one or more of cisplatin and capecitabine, 5-fluorouracil, oxaliplatin, Irinotecan, docetaxel, paclitaxel, doxorubicin mitomycin C, etoposide, gemcitabine or carboplatin. As further outlined herein, in one embodiment, the EGFR biomarker is EGFR gene amplification or EGFR overexpression. In this regard, the EGFR gene amplification may comprise an EGFR gene copy number that is higher than a predetermined number. The EGFR overexpression may comprise a level of EGFR RNA, protein, or activity that is higher than a predetermined level. In certain embodiments of the method, the patient has been determined to contain an EGFR biomarker and not a HER2 biomarker. Thus, in one embodiment, the patient is administered with an anti-EGFR agent without an anti-HER2 agent.

Another aspect of the present invention provides a method for determining whether a patient is suitable for an anti-EGFR treatment comprising detecting in a sample of the patient the presence or absence of an EGFR biomarker, wherein the presence of an EGFR biomarker is indicative that the patient is suitable for the anti-EGFR treatment. In some embodiments, the treatment comprises one or more drugs against EGFR, drugs against the signaling pathway downstream of EGFR, drugs against the ligands of EGFR, drugs against a homodimer formed by EGFRs or a heterodimer formed by EGFR and another member of the ErbB receptor family. In some embodiments, the drug is an anti-EGFR agent. In some embodiments, the anti-EGFR agent comprises anti-EGFR antibody. In some embodiments, the anti-EGFR antibody comprises Cetuximab.

A further aspect of the present invention provides a method for providing a lab service comprising, receiving a sample of a patient with gastric neoplasia, conducting a test to detect in the sample the presence or absence of an EGFR biomarker, and providing the test result to the healthcare provider of the patient.

Yet another aspect of the present invention provides a kit comprising a reagent suitable for detection of an EGFR biomarker and an instruction for using the EGFR biomarker for the treatment of gastric neoplasia according to the methods described herein.

In yet another embodiment, the present invention provides methods for providing useful information for predicting, determining, evaluating or monitoring the treatment or efficacy of treatment of gastric neoplasia with an anti-EGFR drug, e.g., with cetuximab. The method includes determining if a patient has an EGFR biomarker.

In yet another embodiment, the present invention provides methods for monitoring responsiveness or efficacy of an anti-EGFR treatment in a subject suffering from gastric neoplasias. In some embodiments, the methods comprise detecting the presence or absence of an EGFR biomarker in a biological sample from the subject. In some embodiments, the EGFR biomarker is EGFR gene amplification and/or EGFR overexpression compared to a predetermined standard level. In some embodiments, the presence of the EGFR biomarker indicates the patient is a responder to the treatment, and the anti-EGFR treatment may have efficacy in the patient, while the absence of the EGFR biomarker indicates the patient is not a responder to the treatment, and the anti-EGFR treatment may not have efficacy in the patient.

In yet another embodiment, the present invention provides methods for determining the treatment regimen for treating a subject suffering from gastric neoplasias. In some embodiments, the methods comprise detecting the presence or absence of an EGFR biomarker in a biological sample from the subject. In some embodiments, the EGFR biomarker is EGFR gene amplification and/or EGFR overexpression compared to a predetermined standard level. In some embodiments, the treatment regimen is determined based on presence or absence of the EGFR biomarker in the biological sample.

In yet another embodiment, the present invention provides methods for predicting the treatment efficacy for a subject suffering from gastric neoplasias. In some embodiments, the methods comprise detecting the presence or absence of an EGFR biomarker in a biological sample from the subject. In some embodiments, the EGFR biomarker is EGFR gene amplification and/or EGFR overexpression compared to a predetermined standard level. In some embodiments, the presence of an EGFR biomarker indicates a positive treatment efficacy.

In yet another embodiment, the present invention provides methods for providing data. In some embodiments, the methods comprise detecting the presence or absence of an EGFR biomarker in a biological sample from a subject suffering from gastric neoplasias. In some embodiments, the methods further comprise providing the information regarding the presence or absence of an EGFR biomarker to a healthcare provider for diagnosis or treatment of the subject. In some embodiments, the methods further comprise receiving the biological sample from the healthcare provider before the detecting step.

In yet another embodiment, the present invention provides methods of providing useful information for monitoring, predicting or determining the treatment efficacy of an anti-EGFR treatment. In some embodiment, the methods comprises detecting the presence or absence of an EGFR biomarker compared to a predetermined standard level in a biological sample from a subject suffering from gastric neoplasias. In some embodiments, the methods further comprise providing the information regarding the presence or absence of an EGFR biomarker to an entity that provides a prediction or determination of the treatment efficacy.

For all the methods described herein, in some embodiments, the baseline level of EGFR activity in a patient is detected before the anti-EGFR treatment. Such baseline level of EGFR activity include, but are not limited to, EGFR gene copy number, transcript abundance, transcript stability, transcription rate, translation rate, post-translation modification, protein abundance, protein stability, and/or protein enzymatic activity, etc. In some embodiments, an increase in the baseline level of EGFR activity in the patient when compared to the predetermined standard level indicates the presence of an EGFR biomarker.

For all the methods described herein, in some embodiments, the biological sample is selected from blood, skin, hair, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, and tissue extract sample or biopsy sample.

BRIEF DESCRIPTION OF THE FIGURES

The invention is more fully appreciated in connection with the following detailed description taken in conjunction with the accompanying drawings, in which.

DETAILED DESCRIPTION OF THE INVENTION

Figure 1A:
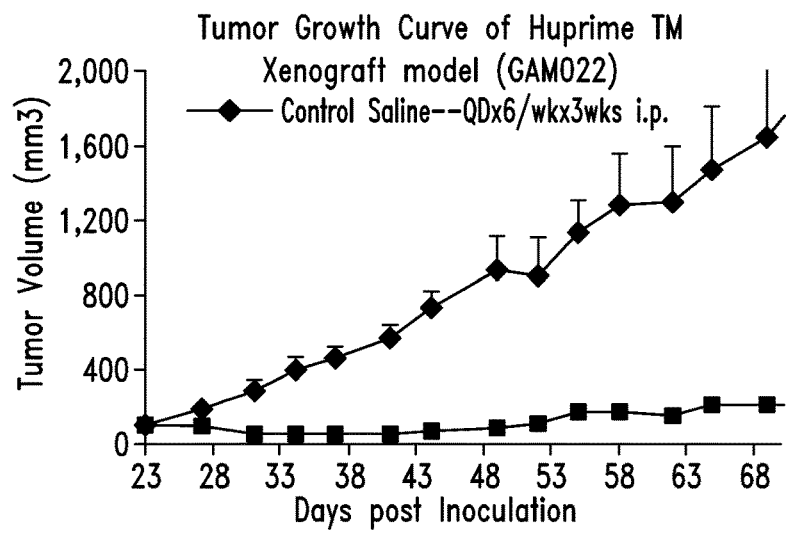
FIG. 1 GC-ADC HuPrime® models responses to cetuximab: Panel A (FIG. 1A): representative tumor growth inhibition by cetuximab of the responders (top three models) and non-responders (bottom three rows of 8 models). Panel B (FIG. 1B): Pharmacodynamic analysis of model GA0022. pERK-IHC analysis of model GA0022 tumors post-cetuximab treatment at time points of 0, 6, 24, and 72 hours. Both IHC images and scores are shown. Panel C (FIG. 1C): The PDX-GC models are sorted by the tumor response to cetuximab (DT/DC). The responders at the right part display higher EGFRmRNAlevel and IHC staining intensity, and the only two cases (GA0075 and GA0152, CN>5) of gene amplification.
Figure 1A:
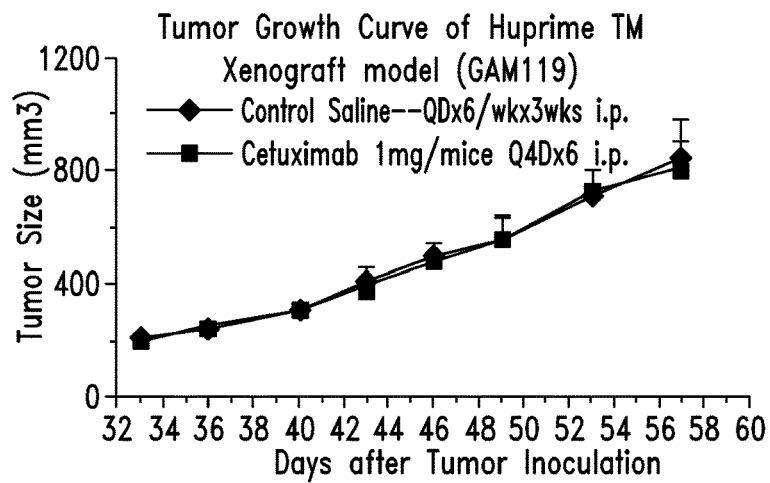
Figure 1A:
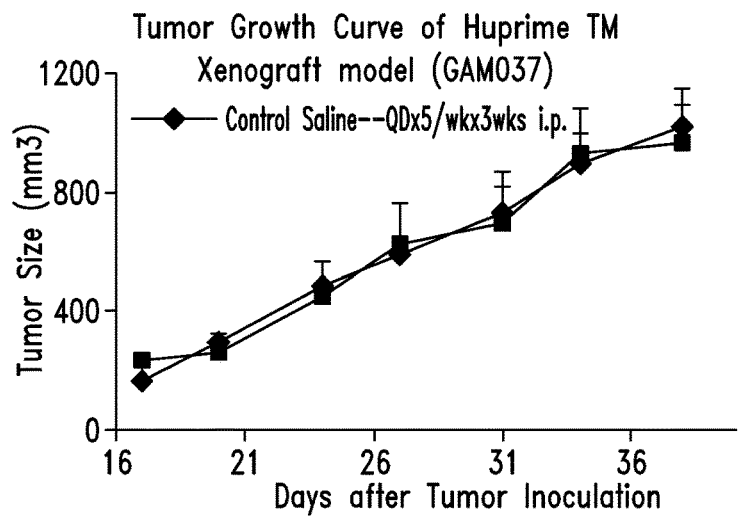
Figure 1A:
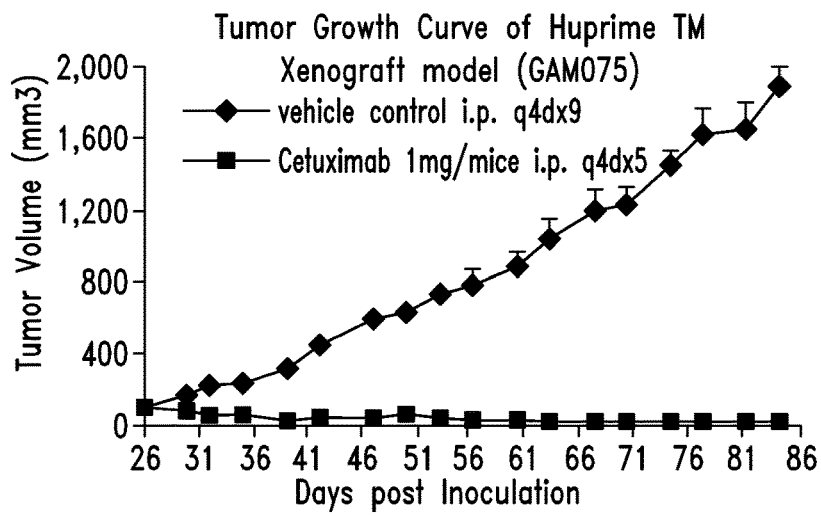
Figure 1A:
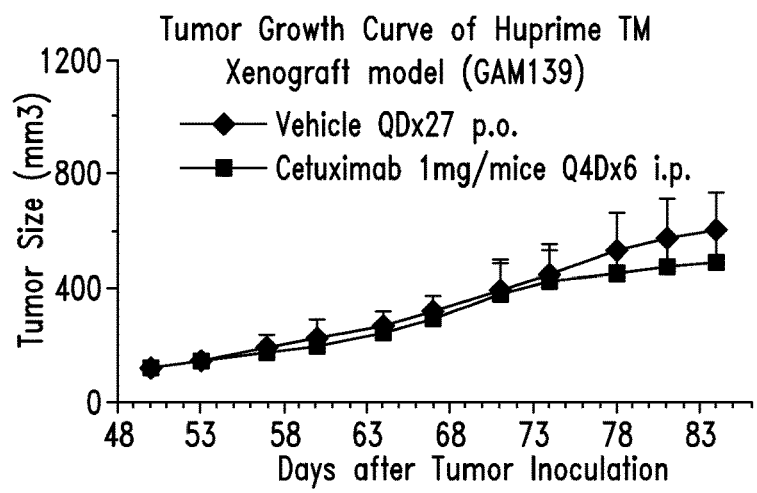
Figure 1A:
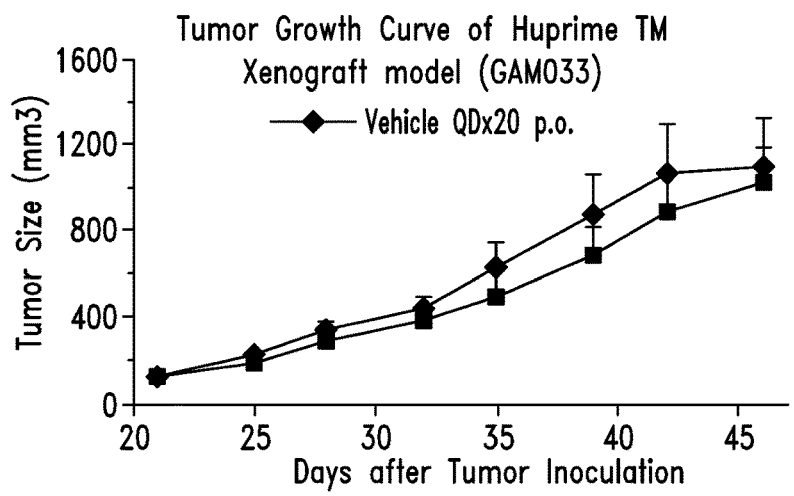
Figure 1A:
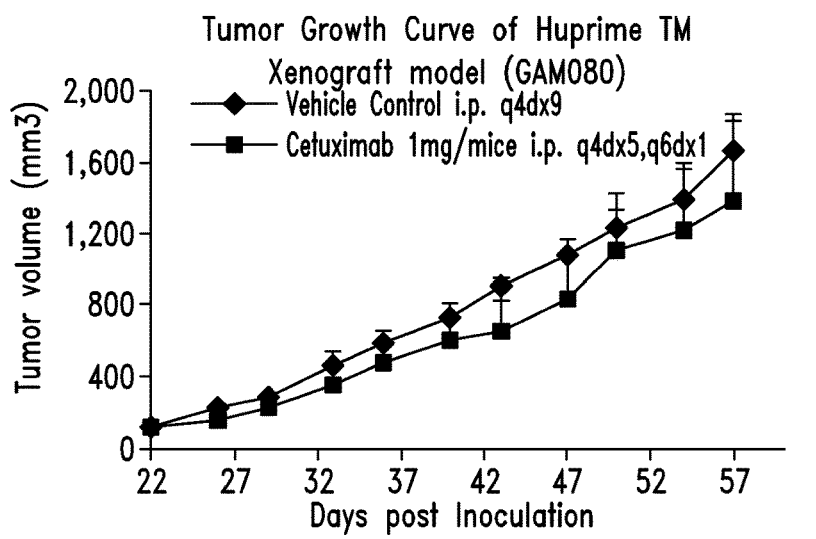
Figure 1A:
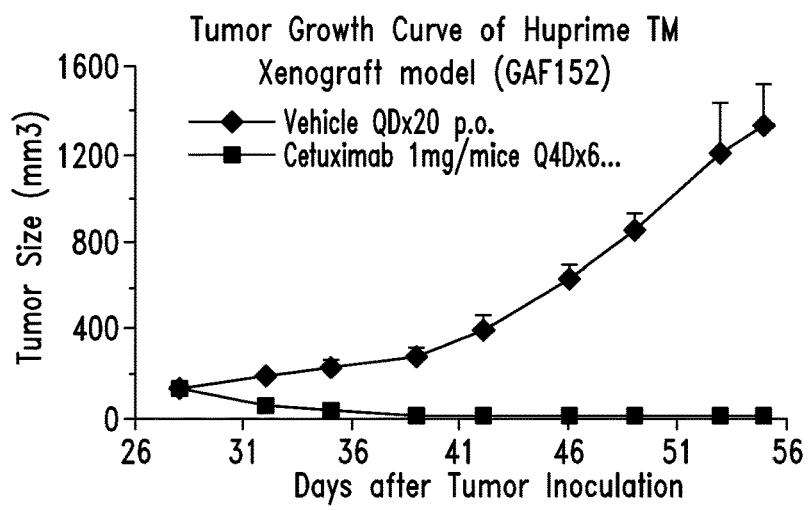
Figure 1A:
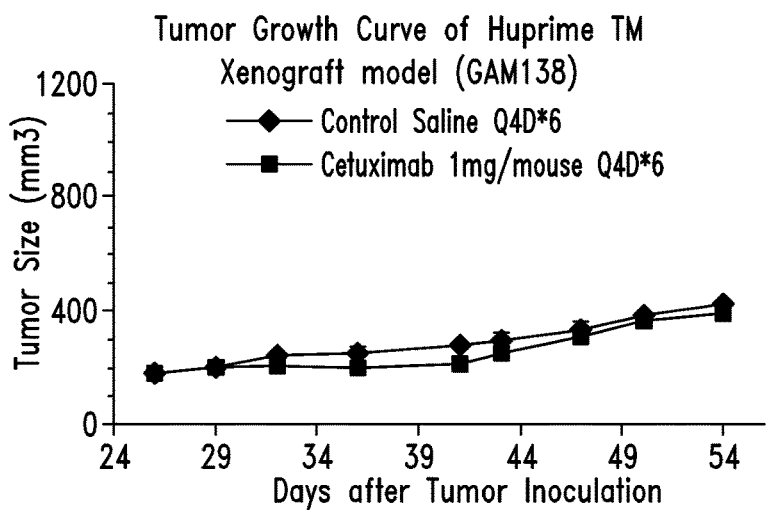
Figure 1A:
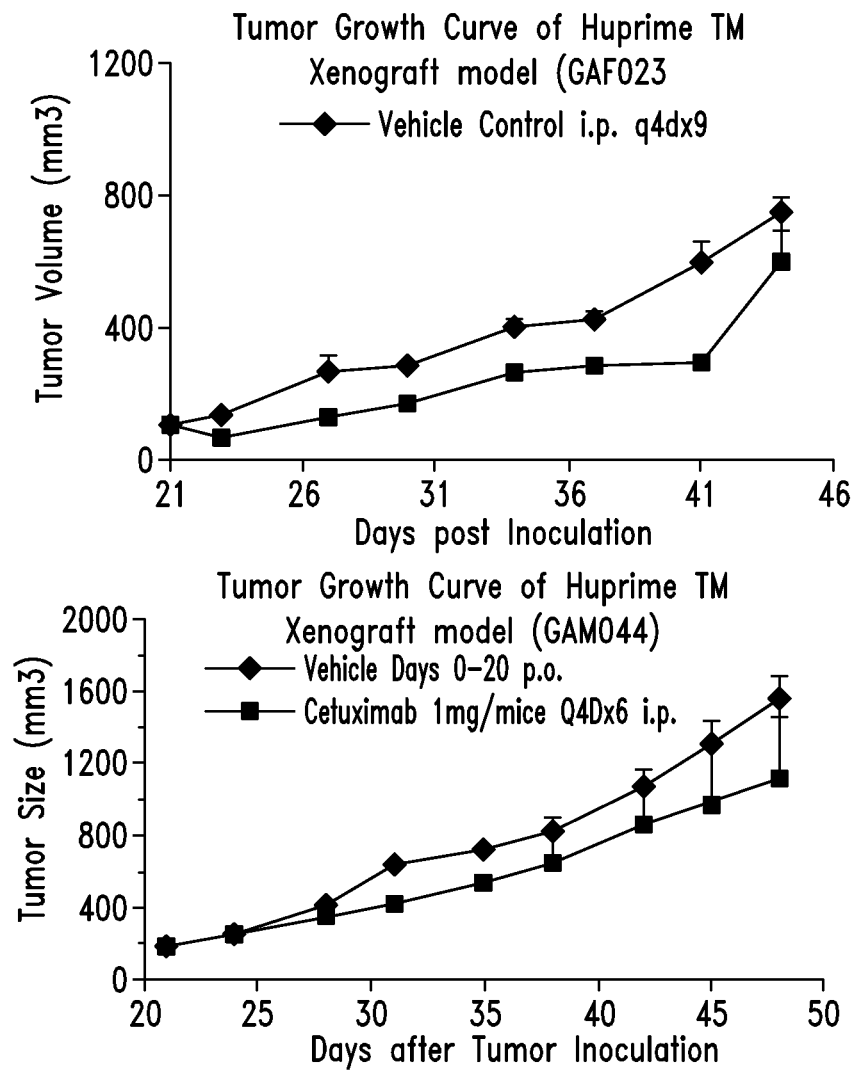

The present invention relates generally to methods for treating gastric neoplasias with an anti-EGFR agent in particular treating patients who have been previously determined to have a specific EGFR biomarker. The present invention permits treatment of patients who have a greater likelihood of responding to the treatment by administering therapeutic agents, i.e., anti-EGFR antibodies to patients who are found to have an amplified gene encoding the EGFR protein or overexpression of EGFR (as measured by mRNA expression, protein expression or activity level). The invention is based, in part, on the discovery that EGFR gene amplification, e.g., as detected by fluorescence in situ hybridization (FISH), by microarray analysis, or by other methods known in the art, or EGFR overexpression, provide a basis for selecting patients for treatment because EGFR gene amplification or EGFR overexpression correlates with response to treatment.

In one aspect, the present invention provides a method for determining whether a patient is suitable for an anti-EGFR treatment comprising detecting in a sample of the patient the presence or absence of an EGFR biomarker, wherein the presence of an EGFR biomarker is indicative that the patient is suitable for the anti-EGFR treatment.

The drug can be any drug that is against epidermal growth factor receptor (EGFR). As used herein, a drug against EGFR refers to a composition which can modify the activity of EGFR, such as a composition that can increase, decrease, eliminate, enhance, delay, reduce, or block the activity of EGFR. In some embodiments, the composition is against EGFR at transcriptional level, translational level, post-translational level, and/or protein level. The composition can specifically target EGFR, or target at least EGFR. In some embodiments, the composition can cause gene suppression and/or gene silencing of EGFR, e.g., knocking down or knocking out EGFR. In some embodiments, the composition can modify EGFR protein activity, such as modifying the EGFR binding activity to its ligand and/or its ability to induce downstream signaling pathways. In some embodiments, the drug is an antagonist or an antibody of the ligand of EGFR, for example, an antagonist or an antibody of epidermal growth factor (EGF), transforming growth factor α (TGFα), HB-EGF, amphiregulin, betacellulin, epigen, and/or epiregulin. In some embodiments, the drug can target to EGFR and/or the ligand and block ligand-receptor binding. In some embodiments, the drug can cause confirmation changes in the receptor and/or the ligand and reducing or inactivating EGFR mediated cell signaling.

In some embodiments, the drug is against a heterodimer formed by EGFR and another member of the ErbB receptor family such as EfbB2/Her2/neu, or a homodimmer formed by two EGFR molecules.

In some embodiments, the drug is against the signaling pathway downstream of EGFR. As used herein, the term "drug against the signaling pathway downstream of EGFR" refers to a composition comprising an agent that can modify the activity of the signaling pathway downstream of EGFR, such as one or more downstream targets of EGFR. EGFR signaling pathway is described in Sechacharyulu et al. (Targeting the EGFR signaling pathway in cancer therapy, Expert Opin Ther Targets, 2012 January; 16(1): 15-31.), Oda et al. (A comprehensive pathway map of epidermal growth factor receptor signaling, Molecular Systems Biology 1:2005.0010), and Development EGFR Signaling Pathway (Pathway Maps, Thomson Reuters, 2012), each of which is incorporated herein in its entirety for all purposes.

In some embodiments, the drug comprises a small molecule. As used herein, the term "small molecule" refers to a molecule having a molecular weight of less than 500 MW, wherein the drug is a non-peptidyl or peptide agent. In some embodiments, the drug comprises a protein or a polypeptide.

In some embodiments, the drug comprises a hybrid molecule. In some embodiments, the drug is an antibody. In some embodiments, the drug is an anti-EGFR antibody. In some embodiments, the drug is an anti-EGFR ligand antibody. In some embodiments, the drug is a humanized anti-EGFR ligand antibody. In some embodiments, the antibody is a monoclonal antibody.

In some embodiments, the drug is an anti-EGFR antibody. In some embodiments, the drug is Cetuximab or functional variants or derivatives thereof. None limiting examples of anti-EGFR antibodies have been described in PCT publication Nos. WO/2011/140151, WO/2007/058823, WO/2011/080209, WO/2010/080463, WO/2012/020059, WO/2011/080209, WO/2011/059762, WO/2011/152525, WO/2011/140254, WO/2010/034441, WO/2011/156617, WO/2005/090407, WO/2013/006547, WO/2008/140493, WO/2011/156617, U.S. Pat. Nos. 5,942,602, 6,129,915, 7,723,484, 7,618,631, 7,598,350, and U.S. Patent Application Publication Nos. 20100166755, 20080274114, 20130142812, 20110158987, 20120107234, 20110117110, 20110287002, 20120149879, 20120282633, 20100009390, 20050238640, 20060154334, 20120231021 and 20130149299, each of which is incorporated herein by reference in its entirety for all purposes.

As used herein, the term "epidermal growth factor receptor" ("EGFR") refers to a gene that encodes a membrane polypeptide that binds, and is thereby activated by, epidermal growth factor (EGF). EGFR is also known in the literature as ERBB, ERBB1 and HER1. An exemplary EGFR is the human epidermal growth factor receptor (see Ullrich et al. (1984) Nature 309:418-425; Genbank accession number NP-005219.2; complete cds AY588246.1). Binding of an EGF ligand activates the EGFR (e.g. resulting in activation of intracellular mitogenic signaling, autophosphorylation of EGFR). One of skill in the art will appreciate that other ligands, in addition to EGF, can bind to and activate the EGFR. Examples of such ligands include, but are not limited to, amphiregulin, epiregulin, TGF-α, betacellulin, and heparin-binding EGF (HB-EGF). Intracellular domain of, a human, EGFR comprises a polypeptide sequence from amino acid adjacent to the transmembrane domain up to COOH-terminus of the EGFR. Intracellular domain comprises, inter alia, tyrosine kinase domain.

As used herein, an "EGFR gene" refers to a nucleic acid that encodes an EGFR gene product, e.g., an EGFR mRNA, an EGFR polypeptide, and the like.

As used herein, an "anti-EGFR agent" refers to any agent capable of directly or indirectly binding to EGFR and inhibiting activation of an EGFR, or modulate the activity of the signaling pathway downstream of EGFR. Anti-EGFR agents include antibodies that bind to an EGFR and inhibit activation of the EGFR, as well as small molecule tyrosine kinase inhibitors or "kinase inhibitors" that inhibit activation of an EGFR. Antibodies to EGFR include IgG; IgM; IgA; antibody fragments that retain EGFR binding capability, e.g., Fv, Fab, F(ab)$_2$, single-chain antibodies, and the like; chimeric antibodies; etc. Small molecule tyrosine kinase inhibitors of EGFR include EGFR-selective tyrosine kinase inhibitors. Small molecule tyrosine kinase inhibitors of EGFR can have a molecular weight in a range of from about 50 Da to about 10,000 Da.

According to the present invention, an "anti-EGFR agent" or "EGFR inhibitor" can be any agent that inhibits (blocks, reduces, antagonizes, decreases, reverses) the expression and/or biological activity of an epidermal growth factor receptor (EGFR), including any EGFR. Therefore, an anti-EGFR agent can include, but is not limited to, a product of drug/compound/peptide design or selection, an antibody or antigen binding fragment thereof, a protein, a peptide, a nucleic acid (including ribozymes, antisense, RNAi and aptamers), or any other agent that inhibits the expression and/or biological activity of an EGFR. For example, known inhibitors of EGFR include the drugs, gefitinib (ZD 1839, Iressa®, AstraZeneca, UK) and erlotinib (OSI 774, Tarceva®, Genentech, USA), and the monoclonal antibody, Cetuximab (Erbitux®, Imclone, Bristol-Myers Squibb). However, the invention is not limited to these specific agents, and can include an agonist of such agents or agents having substantially similar biological activity as these agents. The biological activity or biological action of a protein, such as an EGFR, refers to any function(s) exhibited or performed by a naturally occurring form of the protein as measured or observed in vivo (i.e., in the natural physiological environment of the protein) or in vitro (i.e., under laboratory conditions). Biological activities of EGFR include, but are not limited to, binding to EGF, receptor homo- or heterodimerization, tyrosine kinase activity, and downstream activities related to cellular homeostasis and development.

Tyrosine kinase inhibitors represent a class of therapeutic agents or drugs that target receptor and/or non-receptor tyrosine kinases in cells such as tumor cells. In certain instances, the tyrosine kinase inhibitor is an antibody-based (e.g., anti-tyrosine kinase monoclonal antibody, etc.) or polynucleotide-based (e.g., tyrosine kinase antisense oligonucleotide, small interfering ribonucleic acid, etc.) form of targeted therapy. Preferably, the tyrosine kinase inhibitor is a small molecule that inhibits target tyrosine kinases by binding to the ATP-binding site of the enzyme. Examples of small molecule tyrosine kinase inhibitors include, but are not limited to, gefitinib (Iressa®), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; ST1571), dasatinib (BMS-354825), leflunomide (SU10), vandetanib (Zactima®; ZD6474), pharmaceutically acceptable salts thereof, derivatives thereof, analogs thereof, and combinations thereof. Additional examples of tyrosine kinase inhibitors suitable for use in the present invention include quinazolines (e.g., PD 153035, 4-(3-chloroanilino)quinazoline, etc.), pyridopyrimidines, pyrimidopyrimidines, pyrrolopyrimidines (e.g., CGP 59326, CGP 60261, CGP 62706, etc.), pyrazolopyrimidines, 4-(phenylamino)-7H-pyrrolo[2,3-d]pyrimidines, curcumin (diferuloyl methane), 4,5-bis(4-fluoroanilino)phthalimide, tyrphostines containing nitrothiophene moieties, quinoxalines (see, e.g., U.S. Pat. No. 5,804,396), tryphostins (see, e.g., U.S. Pat. No. 5,804,396), PD0183805, PKI-166, EKB-569, IMC-1C11, Affinitac® (LY900003; ISIS 3521), and the tyrosine kinase inhibitors described in PCT Publication Nos. WO 99/09016, WO 98/43960, WO 97/38983, WO 99/06378, WO 99/06396, WO 96/30347, WO 96/33978, WO 96/33979, and WO 96/33980.

Illustrative anti-EGFR agents are anti-EGFR antibodies, including but not limited to the anti-EGFR antibodies: cetuximab (ERBITUX™), panitumumab (VECTIBIX™), matuzumab, nimotuzumab, antibody 806, Sym004, and MM-151 in their murine, chimeric or humanized versions including their immunologically effective fragments (Fab, Fv) and immunoconjugates, especially immunocytokines Other antibodies (or other binding molecules) specific for the EGFR extracellular domain are known in the art and are contemplated for use herein (see, e.g., U.S. Pat. Nos. 5,459, 061, 5,558,864, 5,891,996, 6,217,866, 6,235,883, 6,699,473, and 7,060,808; European Pat. Nos. EP0359282 and EP0667165).

The term "tumor sample" as used herein means a sample comprising tumor material obtained from a cancerous patient. The term encompasses clinical samples, for example tissue obtained by surgical resection and tissue obtained by biopsy, such as for example a core biopsy or a fine needle biopsy. The term also encompasses samples comprising tumor cells obtained from sites other than the primary tumor, e.g., circulating tumor cells. The term encompasses cells that are the progeny of the patient's tumor cells, e.g. cell culture samples derived from primary tumor cells or circulating tumor cells. The term encompasses samples that may comprise protein or nucleic acid material shed from tumor cells in vivo, e.g. bone marrow, blood, plasma, serum, and the like. The term also encompasses samples that have been enriched for tumor cells or otherwise manipulated after their procurement and samples comprising polynucleotides and/or polypeptides that are obtained from a patient's tumor material.

As used herein, the term "marker" or "biomarker" encompasses a broad range of intra- and extra-cellular events as well as whole-organism physiological changes. A marker may be represent essentially any aspect of cell function, for example, but not limited to, levels or rate of production of signaling molecules, transcription factors, metabolites, gene transcripts as well as post-translational modifications of proteins. Marker may include partial and/or whole genome analysis of transcript levels, rates, and/or stability, and partial and/or whole proteome analysis of protein levels, activity and/or modifications. A signature may refer to a gene or gene product which is up- or down-regulated in a subject to be treated compared to clinically normal subjects. A signature may also refer to a gene or gene product which is up- or down-regulated in a treated subject having the disease compared to an untreated subject. That is, the gene or gene product is sufficiently specific to the treated cell that it may be used, optionally with other genes or gene products, to identify, predict, or detect efficacy of a small molecule. Thus, in some embodiments, a signature is a gene or gene product that is characteristic of efficacy of a compound in a diseased cell or the response of that diseased cell to treatment by the compound.

An "EGFR biomarker" as used herein refers to EGFR gene amplification and/or overexpression of EGFR. Overexpression of EGFR may relate to overexpression as measured by transcript abundance, transcript stability, transcription rate, translation rate, post-translation modification, protein abundance, protein stability, and/or protein enzymatic activity, mRNA, protein and/or protein activity, etc. As used herein, the term "gene activity" refers to gene expression level, RNA activity level, or protein activity level. As used herein, the term "RNA activity level" refers to mRNA abundance, synthesis rate, and/or stability, etc. As used herein, the term "protein activity level" refers to protein abundance, synthesis rate, stability, enzymatic activity, phosphorylation rate, etc.

In some embodiments, the information regarding the biomarkers is obtained from one or more tests. The test can be performed by the subject himself/herself, by a doctor, by a nurse, by a test lab, by a healthcare provider, or any other parties capable of doing the test. The test results containing the biomarker information can be then analyzed by the same party or by a second party, such as the subject himself/herself, a doctor, a nurse, a test lab, a healthcare provider, a physician, a clinical trial personnel, a hospital, a lab, a research institute, or any other parties capable of analyzing the test to determine if the subject is responsive to the drug.

In certain embodiments, threshold level(s) of EGFR gene copy number or overexpression of EGFR can be established, and the EGFR gene copy number or the expression level of EGFR mRNA or protein in a patient's tumor sample can be compared to a "predetermined threshold level" (also referred to as "predetermined level" or "predetermined cut-off value").

A predetermined level, sometimes referred to as a predetermined cut off, of EGFR copy number or expression level may be established using methods known in the art, in particular using Receiver Operator Characteristic curves or "ROC" curves. In practice, ROC curves are typically calculated by plotting the value of a variable versus its relative frequency in "normal" and "disease" populations, and/or by comparison of results from a subject before, during and/or after treatment. In certain embodiments, EGFR expression or gene copy number, or both, in normal samples versus test samples is compared. In some embodiments the EGFR gene copy number is at least 3, 4, 5, 6, 7, 8, 9, 10 or more copies. In some embodiments, the increase is determined by comparing to one or more standard levels or by comparing to levels known in the art as standard levels. Methods of measuring gene amplification, increased expression, increased RNA or DNA levels, as well as determining whether a protein is constitutively active are well known in the art and any such methods can be employed with the present invention.

To determine the presence or absence of an EGFR biomarker, or other biomarker of interest, such as HER2, the signal detected from the reporter group used in a particular test or assay is generally compared to a signal that corresponds to a predetermined cut-off value, or predetermined threshold level. In one embodiment, the predetermined threshold level for the detection of a biomarker is the average mean level obtained from samples from patients without the disease, e.g., without gastric cancer. In general, a sample generating a signal that is three standard deviations above the predetermined threshold level is considered positive for the cancer. In an alternate preferred embodiment, the cut-off value is determined using a ROC, according to the method of Sackett et al., Clinical Epidemiology: A Basic Science for Clinical Medicine, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In some embodiments, a ROC curve representing a patient response to a treatment with an anti-EGFR agent may be used to define the objective function. For example, the objective function may reflect the area under the ROC curve. By maximizing the area under the curve in respect to level of EGFR gene copy number (e.g., EGFR gene amplification) or overexpression of EGFR in patients treated with an anti-EGFR agent, one may maximize whether a patient suffering from a cancer will be responsive to the treatment with an anti-EGFR agent. In some other embodiments, the ROC curve may be constrained to provide an area-under-curve of greater than a particular value. ROC curves having an area under the curve of 0.5 indicate complete randomness, while an area under the curve of 1.0 reflects perfect separation of the two sets. Thus, in certain embodiments, a minimum acceptable value, such as 0.75, may be used as a constraint.

In other embodiments, other features such as use of the point at which the slope of the ROC curve is equal to one; the use of the point at which the product of sensitivity and specificity is a maximum; or combinations of two or more of these ROC-curve features may be used to define the objective function.

In certain embodiments, EGFR overexpression (e.g., mRNA or protein expression) is present at a level that is at least about two-fold, three-fold, four-fold, five-fold, six-fold or higher in tumor tissue than in normal tissue of the same type from which the tumor arose.

In some embodiments, increased levels of EGFR gene copy number or overexpression of EGFR, or both, in the tumor sample relative to a predetermined threshold level are indicative that a patient suffering from a cancer will be responsive to the treatment with an anti-EGFR agent. In some embodiments, decreased levels of EGFR gene copy number in the tumor sample relative to the predetermined threshold level are indicative that a patient suffering from a cancer will be non-responsive to the treatment with an EGFR inhibitor.

The present invention also relates in part to the observation that HuPrime models having an EGFR biomarker (overexpression and/or gene amplifications) do not also have a HER2 biomarker (over-expression and/or gene amplification), and vice versa, i.e. no over-expression (gene amplification) of both EGFR and HER2 was observed in a single model (See Examples). Accordingly, in one embodiment, increased levels of EGFR gene copy number or overexpression of EGFR in the tumor sample relative to a predetermined threshold level and the lack of a HER2 biomarker, are used as indicators for selecting a patient for treatment with an anti-EGFR agent. In this regard, the nucleotide sequence of the human tyrosine kinase receptor-type receptor (HER2) gene is also known in the art and can be found, for example, under GenBank Accession Nos. M16789, M16790, M16791, M16792 and M11730 (all incorporated herein by reference). Nucleotide probes and anti-HER2 antibodies are also known in the art and available for use as probes to the HER2 genes and proteins for determining expression levels/activity thereof.

The term "gene copy number" (GCN) is usually defined as the number of genes per genome. The term "EGFR gene copy number" means the ratio of number of EGFR genes per nucleus. In non-tumorigenic or non-neoplastic cells EGFR gene copy number is similar to or less than 2. In tissue sections of non-tumorigenic or non-neoplastic origin, GCN is similar to or less than 2, if detected with in situ hybridization.

The term "increased EGFR gene copy number", "amplified EGFR gene copy number" or "EGFR gene amplification" means that the above-defined ratio in cells of a tumor correlated to a patient is higher or amplified compared to the particular ratio, or threshold level, in cells of a tumor correlated to non-neoplastic cells of the same origin. In one embodiment, the ratio, or threshold level, (number EGFR gene/nucleus) is greater than 2 or 3 or 4 or 5 or 6 or 7. In another embodiment, said ratio or threshold level is similar to or greater than 4. In certain embodiments the term increased or amplified EGFR gene copy number means GCN greater than the EGFR gene copy number in non-tumorigenic or non-neoplastic cells. In certain embodiments, EGFR GCN, or threshold level, may be more than 4, such as 4.5, 5, 5.5, 6, 6.5, 7, 7.5, 8, 8.5, 9, 9.5, 10, 10.5, 11, 11.5, 12, 12.5, 13, 30.5, 14, 14.5, 15, 50.5, 16 or more. In certain embodiments, EGFR GCN, or threshold level, may be less than 4, such as 3.5, 3, or 2.5.

In some embodiments, EGFR gene copy number similar to or greater than 4 identifies a patient suffering from a cancer who is likely to be responsive to the treatment with –EGFR agent.

According to these afore-mentioned values applicable to an "increased" or "amplified" EGFR gene copy number, the ratio values for a relatively decreased or lower or non-amplified copy number presented by tumor cells of patients, which do not or do not effectively or positively respond, or are non-responsive, to the treatment with EGFR inhibitors or anti-EGFR antibodies are less than 2. In one embodiment, said ratio, or threshold level, is less than 4. In some embodiments, EGFR gene copy number less than 4 identifies a patient suffering from a cancer and who is likely to be non-responsive to the treatment with an anti-EGFR agent.

Methods for determining the presence of an EGFR biomarker, e.g. gene amplification or overexpression of EGFR, or other biomarker of interest (e.g., a HER2 biomarker) include gene expression profiling. Such methods include methods based on hybridization analysis of polynucleotides, methods based on sequencing of polynucleotides, and proteomics-based methods. Exemplary methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and PCR-based methods, such as reverse transcription PCT (RT-PCR) (Weis et al., Trends in Genetics 8:263-264 (1992)). Antibodies may be employed that can recognize sequence-specific duplexes, including DNA duplexes, RNA duplexes, and DNA-RNA hybrid duplexes or DNA-protein duplexes. Next generation sequencing, qPCR, qcPCR, and digital PCR may also be used for determining EGFR expression levels.

Methods for detecting the levels of nucleic acids, such as RNA or DNA have been well described and are well known to those of skill in the art. Methods for detecting RNA can include but are not limited to RT-PCR, northern blot analyses, gene expression analyses, microarray analyses, gene expression chip analyses, hybridization techniques (including FISH), expression beadchip arrays, and chromatography as well as any other techniques known in the art. Methods for detecting DNA can include but are not limited to PCR, realtime PCR, digital PCR, hybridization (including FISH), microarray analyses, SNP detection assays, SNP genotyping assays and chromatography as well as any other techniques known in the art.

Methods for detecting proteins and polypeptides can include but are not limited to spectrophotometric determination of protein concentration, quantitative amino acid analysis, protein concentration assays, chromatography assays, western blot analyses, gel electrophoresis, (followed by staining procedures including but not limited to Coomassie Blue, Silver stain, Syber Green, Syber Gold), hybridization, multiplex cytokine assays, immunoassays, ELISA, bicinchoninic acid (BCA) protein assays, Bradford protein assays, and Lowry protein assays as well as any other techniques known in the art. Protein detection can also include detecting the levels of stable or active proteins and methods such as kinetic assays, kinase assays, enzyme assays and post-translation modification assays (for example, assays for determining phosphorylation and glycosylation state) can also be employed.

As used herein, the term "predetermined standard level" or "predetermined activity profiles" refers to standardized data or data set representing the average, representative features or characteristics of one or more biomarkers in a specific population. Such features or characteristics include, but are not limited to, transcript abundance, transcript stability, transcription rate, translation rate, post-translation modification, protein abundance, protein stability, and/or protein enzymatic activity, etc. In some embodiments, the specific population of subjects are consisting of about 5, about 10, about 20, about 50, about 100, about 200, about 300, about 400, about 500, about 1000, about 5000, about 10K, or more individual subjects. The predetermined activity profile can be a standardized data or data set collected before, during, or after the specific population of subjects has been all exposed to a drug. In some embodiments, the specific population is consisting of clinically normal subjects. As used herein, the term "clinically normal subject" refers to a subject without, or substantially without the symptoms associated with gastric neoplasias. Predetermined standard levels can be defined using a variety of methods known to those of skill in the art. Generally, standard levels for a biomarker are determined by determining the level of an EGFR biomarker in a sufficiently large number of samples obtained from normal, healthy control subjects. In some embodiments, standard level information can be obtained from publically available databases, as well as other sources. (See, e.g., Bunk, D. M., Clin. Biochem. Rev., 28(4):131-137 (2007); Suraj Peril, et al., Genome Res. 13: 2363-2371 (2003); Remington: The Science and Practice of Pharmacy, Twenty First Edition (2005).

For methods related to detection, quantitation and comparison of biomarker levels, see, e.g., Current Protocols in Molecular Biology, Ed. Ausubel, Frederick M. (2010); Current Protocols in Protein Science Last, Ed. Coligan, John E., et al. (2010); Current Protocols in Nucleic Acid Chemistry, Ed. Egli, Martin (2010); Current Protocols in Bioinformatics, Ed. Baxevanis, Andreas D. (2010); and Molecular Cloning: A Laboratory Manual, Third Edition, Sambrook, Joseph (2001), all of which are incorporated herein by reference in their entirety EGFR expression levels can also be assessed using any of a variety of available microarrays. In this method, polynucleotide sequences of interest (including cDNAs and oligonucleotides) are arrayed on a substrate. The arrayed sequences are then contacted under conditions suitable for specific hybridization with detectably labeled cDNA generated from mRNA of a test sample. The source of mRNA typically is total RNA isolated from a tumor sample, and optionally from normal tissue of the same patient as an internal control or cell lines. mRNA can be extracted, for example, from frozen or archived paraffin-embedded and fixed (e.g. formalin-fixed) tissue samples. Illustrative microarrays for use herein include, but are not limited to Affymetrix HG-U219 GeneChip or Affymetrix SNP6 arrays (Affymetrix, Santa Clara, Calif.).

In certain embodiments, detection of the EGFR gene copy number or mRNA expression level is accomplished using hybridization assays. Nucleic acid hybridization simply involves contacting a probe (e.g., an oligonucleotide or larger polynucleotide) and target nucleic acid under conditions where the probe and its complementary target can form stable hybrid duplexes through complementary base pairing. As used herein, hybridization conditions refer to standard hybridization conditions under which nucleic acid molecules are used to identify similar nucleic acid molecules. Such standard conditions are disclosed, for example, in Sambrook et al., Molecular Cloning: A Laboratory Manual, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are known to the skilled artisan.

Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

The hybridized nucleic acids are detected by detecting one or more labels attached to the sample nucleic acids. The labels may be incorporated by any of a number of means well known to those of skill in the art.

In one embodiment, EGFR gene copy number is detected using CFISH analysis. FISH (dual-color) procedures can be performed using commercially available reagents and methods, such as those described in the examples herein. (see, e.g., Abbott PathVysion EGFR DNA Probe Kit (Abbott, Downers Grove, Ill.). In certain embodiments, the labeled probe used for such FISH analysis comprises Spectrum Orange fluorophore-labeled EGFR (303 kb) specific for the EGFR gene locus on chromosome 7p12, and/or the Spectrum Green fluorophore-labeled chromosome enumerator probe (5.4 kb) targeted to the α-satellite DNA sequence located at the centromeric region of chromosome 7 (CEP7; 7p11.1-q11.1).

Many conventional detection methods utilize enzymes. The types of enzyme substrates popularly used for sensitive detection are typically colorimetric, radioactive, or fluorescent. Conventional colorimetric substrates produce a new color (or change in spectral absorption) upon enzyme action on a chromogenic substrate. This type of detection is advantageous in that the chromogens produced are easily detected by light-based microscopy or with spectral equipment. The cost of equipment for detection is also generally less than with other methods; for example in pathology, the brown color produced by the enzyme horseradish peroxidase acting on the substrate 3,3'-diaminobenzidine (DAB), requires only a simple bright field light microscope for observation of biopsied sections. Other chromogens which can be used in conjunction with horseradish peroxidase include, but are not limited to, 3-Amino-9-ethylcarbazole (AEC) and Bajoran Purple. Other chromogens which can be used in conjunction with alkaline phosphatase include, but are not limited to, Fast Red and Ferangi Blue. Numerous chromogens are available to a person having ordinary skill in the art, and are commercially available through catalogs provided by companies such as Thermo Fisher Scientific.

Various labels used in detection methods include fluorescent dyes (e.g., fluorescein isothiocyanate, Texas red, rhodamine, and the like), and enzymes (e.g., LacZ, CAT, horseradish peroxidase, alkaline phosphatase, .beta.-galactosidase, and glucose oxidase, acetylcholinesterase and others, commonly used as detectable enzymes), or members of a binding pair that are capable of forming complexes such as streptavidin/biotin, avidin/biotin or an antigen/antibody complex including, for example, rabbit IgG and anti-rabbit IgG; fluorophores; light scattering or plasmon resonant materials such as gold or silver particles or quantum dots; or radiolabels; and probes labeled with any other signal generating label known to those of skill in the art, as described, for example, in the 6.sup.th Edition of the Molecular Probes Handbook by Richard P. Hoagland. In certain embodiments, the labeled probe comprises Spectrum Orange fluorophore-labeled EGFR (303 kb) specific for the EGFR gene locus on chromosome 7p12, and/or the Spectrum Green fluorophore-labeled chromosome enumerator probe (5.4 kb) targeted to the α-satellite DNA sequence located at the centromeric region of chromosome 7 (CEP7; 7p11.1-q11.1).

In certain embodiments, the hybridizing nucleic acids, such as the EGFR gene or fragment thereof, are detected by metal labels or "enzymatic metallography" and most preferably, in the context of a silver in situ hybridization (SISH) assay (see e.g. patent publication US20080299555 A1). In particular, the enzymatic metallography allows detection of a single copy of a target gene in a chromosome by a conventional bright field microscope without requiring oil immersion. SISH also enables detection of gene copies with a resolution that allows for individual enumeration of signals, such as discrete metal deposit dots for individual gene copies. In one embodiment, the invention allows for detection of at least 2, 3, 4, 5, 6, 7, 8, 9, 10, 11, 12, 13, 14, 15 or more copies of EGFR gene in human chromosome 7 in a nucleus, as discrete metal deposit dots.

The copy number of genes and chromosomes in tumor cells according to the invention can be measured, for example using FISH or SISH assays, in nuclei, and the protein expression can be evaluated, for example in immunohistochemistry assays, in tumor cell nuclei, cytoplasm and/or membranes. These tests, e.g., FISH, SISH and immunohistochemistry, as well as other detection methods, can be performed in primary tumors, metastatic tumors, locally recurring tumors, or other tumoral settings. The tumor specimens can be fresh, frozen, fixed or otherwise preserved.

The nucleotide sequence of the human epidermal growth factor receptor (EGFR) gene is known in the art and can be found under GenBank Accession No. AY588246 (incorporated herein by reference), for example. Nucleotide probes are also known in the art and available for use as probes to detect EGFR genes. For example, such a probe for detecting EGFR and chromosome 7 centromere sequences is available (e.g., LSI EGFR SpectrumOrange/CEP 7 SpectrumGreen probe (Vysis, Abbott Laboratories).

Protein expression can be detected in suitable tissues, such as tumor tissue and cell material obtained by biopsy. For example, the patient tumor biopsy sample, which can be immobilized, can be contacted with an antibody, an antibody fragment, or an aptamer, that selectively binds to the protein to be detected, and determining whether the antibody, fragment thereof or aptamer has bound to the protein. Protein expression can be measured using a variety of methods standard in the art, including, but not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry. In one embodiment, immunohistochemical (IHC) analysis is used to detect protein expression. IHC methods and assessment criteria for detection of protein expression are described in detail, for example, in Hirsch et al., J. Clin. Oncol. 2003, 21:3798-3807.

EGFR gene amplification or overexpression can result in increased EGFR activity. Abnormally high EGFR activation results in phosphorylation of several intracellular substrates, which in turns gives rise to mitogenic signaling as well as other tumor-inducing activities. Accordingly, in certain embodiments, determining the presence of an EGFR biomarker may involve measuring one or more indicators of EGFR biological activity as determined using either a cell proliferation assay, an apoptosis assay, a receptor binding assay, a receptor phosphorylation assay, and the like.

For methods related to detection, quantitation and comparison of biomarker levels, see, e.g., Current Protocols in Molecular Biology, Ed. Ausubel, Frederick M. (2010); Current Protocols in Protein Science Last, Ed. Coligan, John E., et al. (2010); Current Protocols in Nucleic Acid Chemistry, Ed. Egli, Martin (2010); Current Protocols in Bioinformatics, Ed. Baxevanis, Andreas D. (2010); and Molecular Cloning: A Laboratory Manual, Third Edition, Sambrook, Joseph (2001), all of which are incorporated herein by reference in their entireties.

Another aspect of the present invention provides a method for providing a lab service comprising receiving a sample of a patient with gastric neoplasia, conducting a test as described herein to detect in the sample the presence or absence of an EGFR biomarker, and providing the test result to the healthcare provider of the patient.

The present invention also provides kits comprising a reagent suitable for detection of an EGFR biomarker and an instruction for using the EGFR biomarker for determining treatment options for patients with gastric neoplasia according to the methods described herein. Such kits typically comprise two or more components necessary for performing a diagnostic assay. Components may be compounds, reagents, containers and/or equipment. For example, one container within a kit may contain a monoclonal antibody or fragment thereof that specifically binds to EGFR (and/or in certain embodiments, HER2 protein). Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding EGFR (and/or HER2) protein in a biological sample, or for the detection of EGFR gene amplification. Such kits generally comprise at least one oligonucleotide probe or primer, as described above, that hybridizes to the EGFR DNA or to a polynucleotide encoding the EGFR protein. Such an oligonucleotide may be used, for example, within a PCR or hybridization assay. Additional components that may be present within such kits include a second oligonucleotide and/or a diagnostic reagent or container to facilitate the detection of a polynucleotide encoding EGFR or HER2 protein.

Methods for obtaining biological samples are well known in the art and any standard methods for obtaining biological samples can be employed. Biological samples that find use with the methods of the present invention include but are not limited to serum, blood, plasma, whole blood and derivatives thereof, skin, hair, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, and tissue extract sample or biopsy. (See, e.g., Clinical Proteomics: Methods and Protocols, Vol. 428 in Methods in Molecular Biology, Ed. Antonia Vlahou (2008).) In one embodiment, the biological sample of the present invention includes any cell or tissue samples of the esophagus, e.g., on site or circulating or migrating cells of esophageal cancer. In another embodiment, the biological sample of the present invention includes any extract or partial or whole fractionation of cell or tissue samples of the esophagus, e.g., on site or circulating or migrating cells of esophageal cancer.

Pharmaceutical Compositions and Methods of Treatment

The present invention provides methods for treating gastric neoplasia comprising administering to a patient in need of such treatment a therapeutically effective amount of anti-EGFR agent as described herein, wherein the patient has been determined to contain an EGFR biomarker. As used herein, the term "effective amount" refers to the amount of one or more compounds that renders a desired treatment outcome. An effective amount may be comprised within one or more doses, i.e., a single dose or multiple doses may be required to achieve the desired treatment endpoint. As used herein, the term "therapeutically effective amount" as used herein, refers to the level or amount of one or more agents needed to treat a condition, or reduce or prevent injury or damage, optionally without causing significant negative or adverse side effects. For instance, a therapeutically effective amount includes an amount of a pharmaceutical formulation including for example one or more compounds that can modulate the EGFR pathway sufficient to produce a desired therapeutic outcome (e.g., reduction of severity of a disease or condition). In one embodiment, the gastric neoplasia is gastric adenocarcinoma. The methods described herein include methods for treating any type of gastric cancer, including intestinal and diffuse gastric adenocarcinoma, gastrointestinal stromal tumor (GIST), gastrointestinal leiomyosarcoma, gastrointestinal carcinoid and gastrointestinal lymphoma, where the patient has been determined to contain an EGFR biomarker as defined herein. In certain embodiments, the methods are for treating gastric cancer. In particular embodiments the methods comprise methods for treating EGFR-expressing cancer, such as gastric cancer, wherein the cancer is not esophagogastric adenocarcinoma (OGA) or metastatic colorectal carcinoma. In one embodiment, the present invention provides methods for treating gastric neoplasia comprising administering to a patient in need of such treatment a therapeutically effective amount of anti-EGFR agent as described herein, wherein the patient has been determined to contain an EGFR biomarker and not a HER2 biomarker.

Another embodiment provides a method for preventing metastasis of a gastric cancer including, but not limited to, intestinal and diffuse gastric adenocarcinoma, gastrointestinal stromal tumor (GIST), gastrointestinal leiomyosarcoma, gastrointestinal carcinoid and gastrointestinal lymphoma, where the patient has been determined to contain an EGFR biomarker as defined herein, by administering to a cancer patient a therapeutically effective amount of a herein disclosed anti-EGFR agent (such as an EGFR-specific antibody). In this regard, the method comprises administering an amount of an anti-EGFR agent that, following administration, inhibits, prevents or delays metastasis of a gastric cancer in a statistically significant manner, i.e., relative to an appropriate control as will be known to those skilled in the art. In certain embodiments, the patient has been determined to contain an EGFR biomarker and not a HER2 biomarker.

Thus, in one embodiment, the present invention provides methods for preventing metastasis of a gastric cancer where the patient in need thereof is administered with an anti-EGFR agent without an anti-HER2 agent.

As used herein, the terms "treatment," "treating," and the like, refer to administering an agent, or carrying out a procedure (e.g., radiation, a surgical procedure, etc.), for the purposes of obtaining an effect. The effect may be prophylactic in terms of completely or partially preventing a disease, such as cancer, or symptom thereof and/or may be therapeutic in terms of effecting a partial or complete cure for a disease and/or symptoms of the disease. "Treatment," as used herein, covers any treatment of a disease, such as cancer, in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression or halting progression of the disease.

As used herein in the context of patient response to an anti-EGFR agent treatment, the terms "responsive", "beneficial response," "beneficial patient response," and "clinically beneficial response," "clinical benefit," and the like, are used interchangeably and refer to favorable patient response to a drug as opposed to unfavorable responses, i.e. nonresponsive to a treatment and/or having adverse events. In individual patients, beneficial response can be expressed in terms of a number of clinical parameters, including loss of detectable tumor (complete response, CR), decrease in tumor size and/or cancer cell number (partial response, PR), tumor growth arrest (stable disease, SD), enhancement of anti-tumor immune response, possibly resulting in regression or rejection of the tumor; relief, to some extent, of one or more symptoms associated with the tumor; increase in the length of survival following treatment; and/or decreased mortality at a given point of time following treatment. Continued increase in tumor size and/or cancer cell number and/or tumor metastasis is indicative of lack of beneficial response to treatment.

In a population the clinical benefit of a drug, i.e. its efficacy can be evaluated on the basis of one or more endpoints. For example, in one embodiment, analysis of overall response rate (ORR) classifies as responders those patients who experience CR or PR after treatment with drug. Analysis of disease control (DC) classifies as responders those patients who experience CR, PR or SD after treatment with drug.

As is used herein, the term "progression free survival" refers to the time interval from treatment of the patient until the progression of cancer or death of the patient, whichever occurs first.

As used herein, a responder according to the present invention is an individual who exhibits treatment efficacy (e.g., exhibiting a beneficial clinical response) following an anti-EGFR treatment. A patient is a responder if the patient has been determined to have an EGFR biomarker, who will exhibit a beneficial clinical response following treatment with an anti-EGFR agent.

As used herein, the term "non-responder" or "non-responsive" refers to a patient who does not exhibit treatment efficacy (e.g., a beneficial clinical response) following treatment with an EGFR inhibitor. In certain embodiments, a nonresponder may have been determined to have an EGFR biomarker. In other embodiments, a nonresponder may have been determined not to have an EGFR biomarker.

The phrase "determining the treatment efficacy" or "determining the efficacy of treatment" and variants thereof can include any methods for determining that a treatment is providing a benefit to a subject. The term "treatment efficacy" and variants thereof are generally indicated by alleviation of one or more signs or symptoms associated with the disease and can be readily determined by one skilled in the art. "Treatment efficacy" may also refer to the prevention or amelioration of signs and symptoms of toxicities typically associated with standard or non-standard treatments of a disease, i.e. chemotherapy or radiation therapy for the treatment of cancer. Determination of treatment efficacy is usually indication and disease specific and can include any methods known or available in the art for determining that a treatment is providing a beneficial effect to a patient. For example, evidence of treatment efficacy can include but is not limited to remission of the disease or indication, for cancer this can include but is not limited to a decrease or reduction in tumor size, in tumor metastasis, etc. Further, treatment efficacy can also include general improvements in the overall health of the subject, such as but not limited to enhancement of patient life quality, increase in predicted subject survival rate, decrease in depression or decrease in rate of recurrence of the indication (increase in remission time). (See, e.g., *Physicians' Desk Reference* (2010).)

For the methods of the present invention, the EGFR biomarker can be any in vitro or in vivo indicator for EGFR gene amplification and/or EGFR overexpression, such as EGFR RNA levels, constitutively active EGFR, EGFR activity, EGFR pathway activation or EGFR pathway signaling. In one embodiment, EGFR biomarkers include any form of mutations at the DNA, RNA, or protein level that are associated with EGFR gene amplification and/or EGFR overexpression, such as L858R/T790M double mutations, insertion mutation (exon 20:2319-2320), deletion mutation (exon 19:2236-2350). In another embodiment, EGFR biomarkers include any measurement directly or indirectly associated with EGFR gene amplification and/or EGFR overexpression. In some embodiments, the EGFR biomarker is selected from EGFR gene amplification, increased EGFR expression, increased EGFR RNA levels, constitutively active EGFR and enhanced EGFR pathway activation or enhanced EGFR pathway signaling when compared to a predetermined standard level.

Administration of the anti-EGFR agents described herein, such as anti-EGFR antibodies, in pure form or in an appropriate pharmaceutical composition, can be carried out via any of the accepted modes of administration of agents for serving similar utilities. The pharmaceutical compositions can be prepared by combining an anti-EGFR agent (e.g., antibody) or an anti-EGFR agent-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including, but not limited to, oral, parenteral, nasal, intravenous, intradermal, subcutaneous or topical. Preferred modes of administration depend upon the nature of the condition to be treated or prevented. An amount that, following administration, reduces, inhibits, prevents or delays the progression and/or metastasis of a cancer is considered effective.

An anti-EGFR antibody treatment can include any treatment using anti-EGFR antibody or antibody like therapeutics including without any limitation any molecule with one or more anti-EGFR CDRs. In one embodiment, anti-EGFR antibody treatment includes any approved anti-EGFR antibody, e.g., cetuximab (also known as erbitux) or biosimilar or derivatives thereof, e.g., fully human anti-EGFR antibody, etc. Cetuximab (marketed in North America by ImClone and Bristol-Myers Squibb and in the rest of the world by Merck KGaA) is a recombinant, human/mouse chimeric monoclonal antibody that blocks activation of the epidermal growth factor (EGF) receptor (EGFR). Cetuximab can be given by intravenous infusion for treatment of metastatic colorectal cancer and head and neck cancers. In some embodiments, cetuximab is formulated in a sterile colorless liquid of pH 7.0 to 7.4. In some embodiments, cetuximab is formulated at a concentration of 2 mg/mL in either 100 mg (50 mL) or 200 mg (100 mL). In some embodiments, cetuximab is formulated in single-use vials. In some embodiments, the cetuximab formulation includes 8.48 mg/mL sodium chloride, 1.88 mg/mL sodium phosphate dibasic heptahydrate, 0.41 mg/mL sodium phosphate monobasic monohydrate, and sterile water for injection. Methods and formulations for administering cetuximab are well known by those skilled in the medical art and any well known methods of administering cetuximab, dosing regimens for cetuximab or formulations for cetuximab are contemplated for use with the methods of the present invention. Detailed compositions and methods of using Cetuximab are described in U.S. Pat. Nos. 8,075,916, 7,977,336, 6,217,866, each of which is incorporated by reference in its entirety for all purposes.

In some embodiments, the biomarkers of the present invention can be used together with another biomarker indicating the efficacy of the same drug and/or a different drug which is used to treat a patient suffering from gastric neoplasias.

In some embodiments, the information obtained from the sample can include index values based on the increase or decrease in the EGFR gene amplification or EGFR gene overexpression level. For example, the level of the EGFR gene amplification or EGFR gene overexpression can be assigned an index value based on the increase or the decrease ratio. In some embodiments, the larger the increase or decrease, the larger the index value. In some embodiments, the index values can be compiled as group to generate a composite. In some embodiments, the composite is compared to a predetermined standard. In some embodiments, comparison of the composite to a predetermined standard is indicative of treatment efficacy of treatment with the therapeutic entity. In some embodiments, comparison of the composite to a predetermined standard can be used to modify the treatment regimen of treatment with a therapeutic entity.

In certain embodiments, the amount administered is sufficient to result in tumor regression, as indicated by a statistically significant decrease in the amount of viable tumor, for example, at least a 50% decrease in tumor mass, or by altered (e.g., decreased with statistical significance) scan dimensions. In other embodiments, the amount administered is sufficient to result in clinically relevant reduction in gastric cancer.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The compositions comprising the anti-EGFR agents as described herein may be administered alone or in combination with other known cancer treatments, such as radiation therapy, chemotherapy, transplantation, immunotherapy, hormone therapy, photodynamic therapy, etc. The compositions may also be administered in combination with antibiotics. In some embodiments, the chemotherapeutic includes but is not limited to vinblastine, vincristine, dactinomycin, daunorubicin, doxorubicin, etoposide, mithramycin, paclitaxel, docetaxel, cisplatin, carboplatin, fluorouracil, folinic acid and irinotecan. In some embodiments, the targeted therapeutic includes but is not limited to bevacizumab, trastuzumab, erlotinib, panitumumab, sorafenib, infliximab, adalimumab, basiliximab, daclizumab and omalizumab. In some embodiments, the radiation therapeutic is administered at a dosage of about 40 Gy to about 80 Gy. In some embodiments the dosage is about 50 Gy to about 70 Gy, in some embodiments, the dosage is about 50 Gy to about 65 Gy. In some embodiments, the radiation therapy is administered at a dosage of about 50 Gy, about 55 Gy, about 60 Gy or about 65 Gy.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described anti-EGFR agent in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of an anti-EGFR agent, e.g., an anti-EGFR antibody as described herein, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antimicrobial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. In certain embodiments, physiological saline is a preferred composition. An injectable pharmaceutical composition is preferably sterile.

A liquid pharmaceutical composition intended for either parenteral or oral administration should contain an amount of an anti-EGFR agent, such as an EGFR-specific antibody as herein disclosed such that a suitable dosage will be obtained. Typically, this amount is at least 0.01% of the antibody in the composition. When intended for oral administration, this amount may be varied to be between 0.1 and about 70% of the weight of the composition. Certain oral pharmaceutical compositions contain between about 4% and about 75% of the antibody. In certain embodiments, pharmaceutical compositions and preparations according to the present invention are prepared so that a parenteral dosage unit contains between 0.01 to 10% by weight of the antibody prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody of the invention and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises an anti-EGFR agent, such an EGFR-specific antibody as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with an antibody composition so as to facilitate dissolution or homogeneous suspension of the antibody in the aqueous delivery system.

The compositions may be administered in a therapeutically effective amount, which will vary depending upon a variety of factors including the activity of the specific compound (e.g., an EGFR-specific antibody) employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compositions comprising an anti-EGFR agent, such as an EGFR-specific antibody, may also be administered simultaneously with, prior to, or after administration of one or more other therapeutic agents. In one embodiment, the present invention provides methods for treating gastric neoplasia comprising administering to a patient in need of such treatment an effective amount of a combination of two or more anti-EGFR agents, wherein the patient has been determined to contain an EGFR biomarker. In this regard, the treatment may comprise an effective amount of a combination of two or more anti-EGFR agents selected from cetuximab, panitumumab, nimotuzumab, antibody 806, Sym004, MM-151, and other anti-EGFR agents described herein.

In one embodiment, the present invention provides methods for treating gastric neoplasia comprising administering to a patient in need of such treatment an effective amount of an anti-EGFR agents, wherein the patient has been determined to contain an EGFR biomarker, in combination with a standard of care treatment for gastric cancer. Standard treatments for gastric cancer include: surgery, radiation therapy, or chemotherapy, or a combination of these treatments. Surgery may comprise surgery to remove the affected part of the stomach and nearby lymph nodes or in certain cases can include gastrectomy. Currently, there is no single standard chemotherapy treatment plan used worldwide for the treatment of gastric cancer. However, chemotherapy treatments may include the combination of at least two drugs, fluorouracil (5-FU, Adrucil) and cisplatin (Platinol). Other drugs similar to 5-FU (such as capecitabine or Xeloda) and similar to cisplatin (such as oxaliplatin or Eloxatin) appear to be equivalent. Other drugs commonly used include docetaxel (Taxotere), paclitaxel (Taxol), irinotecan (Camptosar), and epirubicin (Ellence).

As would be understood by the skilled person, combination therapy may include administration of a single pharmaceutical dosage formulation which contains an anti-EGFR agent and one or more additional active agents, as well as administration of compositions comprising anti-EGFR agents and each active agent in its own separate pharmaceutical dosage formulation. For example, an anti-EGFR antibody as described herein and the other active agent can be administered to the patient together in a single oral dosage composition such as a tablet or capsule, or each agent administered in separate oral dosage formulations. Similarly, an anti-EGFR antibody as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising anti-EGFR agents, such as antibodies, and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of a composition comprising an anti-EGFR agent, such as an EGFR-specific antibody, in combination with one or more other therapeutic agents. Such therapeutic agents may be accepted in the art as a standard treatment for a particular disease state as described herein, such as a cancer, in particular gastric cancer. Exemplary therapeutic agents contemplated include cytokines, growth factors, steroids, NSAIDs, DMARDs, anti-inflammatories, chemotherapeutics, radiotherapeutics, or other active and ancillary agents.

In certain embodiments, an anti-EGFR agent, such as an anti-EGFR antibody, may be administered to a patient identified as having an EGFR biomarker, in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and docetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; oxaliplatin; Irinotecan; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the anti-EGFR agents described herein. In one embodiment, a patient identified as having an EGFR biomarker is administered an anti-EGFR agent with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Exemplary NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol of proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®)), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

The compositions comprising anti-EGFR agents described herein, such as EGFR-specific antibodies, may be prepared with carriers that protect the antibody against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Example 1

EGFR Gene Amplification and Overexpression are Predictive Biomarkers for Response to Cetuximab Treatment in Gastric Adenocarcinoma This example describes the results of a random cetuximab trial that was conducted in a cohort of fully molecularly annotated (expression and mutation profiling) naïve Asian gastric adenocarcinoma (GC-ADC) patient derived xenografts (PDX) to identify responders and non-responders, followed by discovery of predictive biomarker.

Introduction and Summary

Patient derived xenograft (PDX), without any in vitro manipulation, mirrors patients' histopathological and genetic profiles[9-14]. It has improved predictive power as preclinical cancer models, and enables the true individualized therapy and discovery of predictive biomarkers. The models are also called as "Avatar mice" or "xenopatients", and the large collection of them can potentially reflect the diversity of tumors in patients. Due to the extensive diversity of cancer patient populations, successfulness of the clinical trial largely relies on the inclusion of the likely responders who express the intended target and have the correct genetic profiles, and exclusion of non-responders. These models thus can be used to test investigational targeted drugs by modeling clinical trial format.

A large collection of gastric adenocarcinoma (GC-ADC) PDX called GC-ADC HuPrime® models (similar NSCLC-HuPrime was previously described)[15] were established. A cohort of 19 GC HuPrime® were tested to evaluate the tumor response to cetuximab and it was found that a subset of the GC-ADC with EGFR gene amplification and over-expression responded well to cetuximab. This observation suggested that EGFR gene copy and/or over expression could serve as a potential practical single biomarker to predict patient response to cetuximab, a situation similar to that of HER2/Herceptin® scenario in GC-ADC. A prospective clinical study using EGFR gene copy number as a patient selection criterion is warranted to further confirm the observation and could lead to ultimate regulatory approval of cetuximab as GC-ADC treatment.

Findings:

Among the 19 PDX GC models tested, 4 models (21%) responded to cetuximab (defined by $\Delta T/\Delta C > 20\%$). The expression profiling and copy number variation analysis revealed that all the 4 responders have amplified EGFR gene and/or corresponding high EGFR expression, in contrast to the 15 non-responders ($\Delta T/\Delta C > 20\%$). This result is consistent with an observation made in EXTRA, a phase II trial where all 4 patients with EGFR amplification are responders. These results suggested that EGFR gene amplification and/or high expression are the key oncogenic driver for this subset of GC-ADC, which is not typical for NSCLC and CRC.

Interpretation:

EGFR gene amplification and over-expression can serve as a single predictive biomarker for cetuximab response in GC-ADC.

Materials and Methods

Patient Samples, Engraftment, Cetuximab Treatment Experiments and Model Characterizations.

Surgically removed fresh GC tumor tissues were used to subcutaneously engraft into 6-8 week old, female Balb/c nude mice (Beijing HFK Bioscience Co. Ltd., Beijing, China) immediately after surgery per procedures described previously[10]. The established tumor models were serially re-engrafted for passage and conducting studies. Access and use of the patient samples were approved by the Ethic Committee of Beijing Cancer Hospital along with the informed consents from the patients. All procedures were performed under a sterilization conditions in Crown Bioscience SFP facility. All the experimental animals that involved in our studies were conducted in strict accordance with the recommendations in the Guide for the Care and Use of Laboratory Animals of the National Institutes of Health. The protocol was approved by the Committee on the Ethics of Animal Experiments of Crown Bioscience, Inc. (Crown Bioscience IACUC Committee).

The procedure for evaluating tumor response to cetuximab in PDX models was detailed described previously[15,17]. The tumor growth was monitored twice weekly, and ° $\Delta T/\Delta C$ value were calculated for assessing tumor response to cetuximab ($\Delta T$=tumor volume change in the treatment group and $\Delta C$=tumor volume change in control group).

Model characterizations, including expression profiling using Affy U219, SNP6, IHC, qPCR, oncogene mutation analysis, have all been detailed described previously[15,17].

Evaluation of Antitumor Activity.

When tumor volume reaches 100-150 mm, the mice were randomly grouped into two groups of five mice with similar average tumor volume. Immediately after grouping, the control group was treated with vehicle (PBS, weekly intraperitoneal injection or IP for 2 weeks), and the treatment groups were injected with cetuximab (weekly IP injection for 2 weeks, 50 mg/kg, Merck KGaA). The tumor growth was monitored twice weekly, and DT/DC value was calculated for assessing tumor response to the treatment (DT 5 tumor volume change in the treatment group and DC 5 tumor volume change in the control group). The total number of the mice for xenograft is 200 (10 mice/model for 20 PDX models).

EGFR IHC Analysis of GC Tumors.

Standard immunohistochemistry (IHC) was used to analyze tumor tissues from the PDX xenograft models. Briefly, the tissues were fixed in 10% neutral buffered formalin and embedded in paraffin per standard histological procedures. After deparaffinization and rehydratation, 3-mm thick tissue sectionswere pretreated in 0.01 Msodium citrate, pH 6.0 solution at 95uCfor 30 min, followed by staining with rabbit anti-human EGFR antibody (Cell Signaling, Boston, USA) at final dilution 15200. Positive staining was detected using Detection System HRP Polymer Kit (Lab Vision, Fremont, USA). DAB was used as the chromogenic substrate, and sections were counterstained with Gill's hematoxylin (Fisher Scientific, Fair Lawn, N.J.). The test specimens were then scored independently by three investigators in a blinded fashion per following criteria recommended by Shia et al in 2005: Score 0 is when there was no specific membrane staining within the tumor, and positive when there was any staining of tumor cell membrane above background level. The positive cases were further classified into 1+, 2+, and 3+ based on the staining intensity of the membrane. Areas of most intensity were identified by scanning tumor sections at low power (1003), and then images were photographed at high magnification (4003) using Olympus BX51 microscopy system with DP71 digital camera (Olympus, Melville, N.Y.).

Gene Expression Profiling and Gene Copy Number Analysis of GC-PDX.

Fresh GCPDX tumor tissues were collected from the tumor-bearing mice, snap-frozen and stored at 280 uC before being used for genetic and genomic analysis. For gene profiling analysis, the total RNA was isolated from the frozen tissues using Trizol (Invitrogen, Carlsbad, Calif.) per the manufacturer's instructions, and purified using RNeasy mini columns (Qiagen). RNA quality was assessed on a Bioanalyzer (Agilent). Only RNA samples with high quality (RIN. 8) were used for expression profiling assays on Affymetrix HG-U219 array plates following standard protocol (GenChip® 3'IVT Express Kit User Manual, P/N 702646 Rev. 8, Affymetrix). Raw CEL data sets of all samples were normalized by RMA algorithm. Probe set intensity was expressed as log(2) transformed values. For CNV assay using Affymetrix SNP6.0 chips, genomic DNA was isolated and purified using Genomic DNA Tissue and Blood Isolation Kit (Qiagen) following manufacturer's instruction. DNA processing and chip hybridization were performed following standard Affymetrix protocol (Genome wide snp6_manual, Affymetrix). Raw CEL data were QC-ed and filtered to remove low call-rate samples, and gene copy number analysis were performed by PICNIC and/or PennCNV methods. For all of the samples, the relative EGFR gene expression level was determined by quantitative RT-PCR. Extracted mRNA was subjected to amplification using human EGFR specific primers by TaqMan q-PCR. The human GAPDH gene was used as a reference. TaqMan probes and primers for EGFR (assay ID: Hs01076078_m1), GAPDH (Assay ID: Hs99999905_m1) were obtained from Applied Biosystems. The raw data generated by the system were processed using the DCT relative quantification. DCT5 (CT value of target gene)–(CT value of reference gene). DCT values were then converted into intensity value (relative mRNA level 5 2' (2DCT). Also, EGFR gene copy numbers were determined by quantitative PCR. Briefly, the same genomic DNAs were subjected to amplification by TaqMan q-PCR. The primers for EGFR (assay ID: Hs04960197_cn) and RNase P as endogenous reference (part number 4401631) were purchased from Applied Biosystems. The raw data was transferred to CopyCaller software and analyzed.

EGFR Mutation Analysis.

Gene hotspot analyses of common oncogenes associated with resistance to cetuximab such as EGFR (Exon18;19;20; 21), KRAS (Exon2;3;4), BRAF (Exon15;V600E), c-MET (Exon14;16;17;18;19;21), PI3KC (Exon1; 9;20) were carried out to identify the mutations in the tumors. Briefly, genomic DNA was extracted from the tissues using kit mentioned above according to the manufacturer's instructions. Primers used for mutation analyses are shown in Table 5. Polymerase chain reaction was performed in 50 mL reaction mixtures containing: 100 ng of genomic DNA, 5 mL 103PCR buffer, 0.2 mM each of primers, 0.2 mM 43 dNTPs and 1 mL TaqE. Reaction was carried out for 40 amplification cycles. The amplified PCR products were gel purified and sequenced by Sanger Automated Sequencer (ABI). The specificity of the primers to human genes had been assured by BLAST search. Sequencing data alignment analysis and mutation identification was performed using BioEdit software.

CFISH Analysis.

FISH (dual-color) procedures were performed using Abbott PathVysion EGFR DNA Probe Kit per the manufacturer's protocol (Abbott, Downers Grove, Ill.). The Spectrum Orange fluorophore-labeled EGFR (303 kb) are specific for the EGFR gene locus on chromosome 7p12, and the Spectrum Green fluorophore-labeled chromosome enumerator probe (5.4 kb) targeted to the α-satellite DNA sequence located at the centromeric region of chromosome 7 (CEP7; 7p11.1-q11.1). Briefly, the FFPE sections were deparaffinized followed by digestion with pepsin and hybridization. The treated slide were denatured and hybridized with probes, followed by counterstaining with 15 μL DAPI/antifade solution and scanning using OLYMPUS BX51 fluorescent microscope (OLYMPUS BX51, Japan) equipped with single band pass filter set to detect DAPI, Rhodamine (7p12) and FITC (chromosome 7) at 1000×.

Statistical Analysis.

The data of tumor volume were evaluated using Student's t-test for two comparisons, and one-way ANOVA test for multiple comparisons. All data were analyzed using SPSS 16.0. $P<0.05$ was considered to be statistically significant. Fisher's Exact Test was used to access the response difference between the EGFR amplified models and non-amplified models (see quantitativeskills.com/sisa/statistics/fisher.htm).

Results

A Subset of GC HuPrime® Models Responds to Cetuximab.

We set out to test a randomly selected cohort of GC-ADC HuPrime® models by conducting a clinical trial-like study for assessing potential cetuximab activities. These models were first established by transplanting surgically removed tumor tissues from GC-ADC patients into immunocompromised Balb/c nude mice via subcutaneous inoculation. The original patient diagnosis and description are summarized in Table 2 and Table 3. Secondly, 19 randomly selected models were subjected to once-weekly cetuximab treatment for 2 weeks (1 mg/mouse or 50 mg/kg). The tumor response to cetuximab is quantified by $\Delta T/\Delta C$[15] and summarized in Table 4. The models can be divided into two categories according to the activities: 4/19 or 21% of GC-ADC HuPrime® responded (nearly complete responsive with $\Delta T/\Delta C<0\%$) to cetuximab treatment; 15/19 or 79% did not (partial or complete resistant with $\Delta T/\Delta C>30\%$). The representative tumor growth inhibition curves of these two categories are shown in FIG. 1A. The quantification of tumor response as measured by $\Delta T/\Delta C$ values are summarized in Table 1A and Table 1B. GA0152 and GA0075 are examples of cetuximab sensitive models, while GA0119 and GA0139 are resistant models. These rather distinct responses seen in GC-ADC models are somewhat in contrast to the responses that were observed in CRC[17] and NSCLC[15] HuPrime® models. Nevertheless, our data suggested that a subset of GC can potentially benefit from cetuximab. It was also worth noting that the 21% responders observed in this GC-ADC study may not necessarily reflect true percentage of potential responders in the GC-ADC patient population due to the less than 100% take-rate of the engraftment (usually between 30 to 50% in our hand) and the possibility of the biased take-rate among the responders or non-responders.

About 50% Responders Display EGFR Gene Amplification.

In order to discover potential predicting markers of cetuximab response, therefore, we performed molecular characterization of these models, including genome-wide copy number variation and transcriptome profiling, First, we interrogated copy number variation of GC-PDXs using Affymetrix genome-wide human SNP6.0 array and PICNIC (Predicting Integral Copy Numbers In Cancer) algorithm. We found that EGFR copy numbers of all four responders are higher than most of those non-responders (Table 1, P=0.002). To further confirm this finding, we assessed EGFR gene copy number by realtime quantitative PCR (q-PCR) and found that all responders have copy number ≥4, while only 2 of 16 (12.5%) non-responders have copy number ≥4. The difference between these two group is significant (P=0.008). The highest value, 15 by SNP6 1 PICNIC analysis and 1040.9 by q-PCR, is from GA0152, which is also the best responder.

Figure 1B:
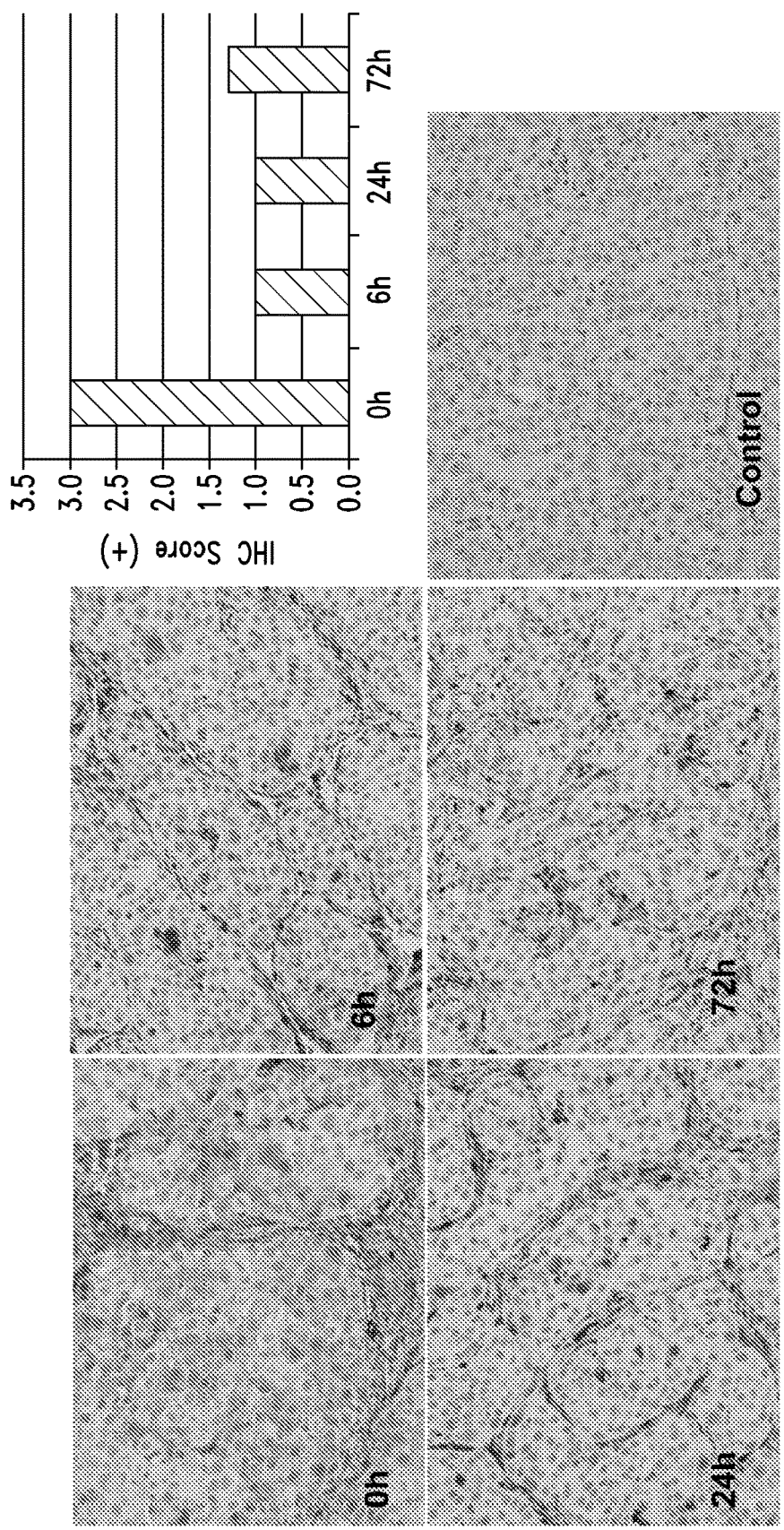
Figure 1C:
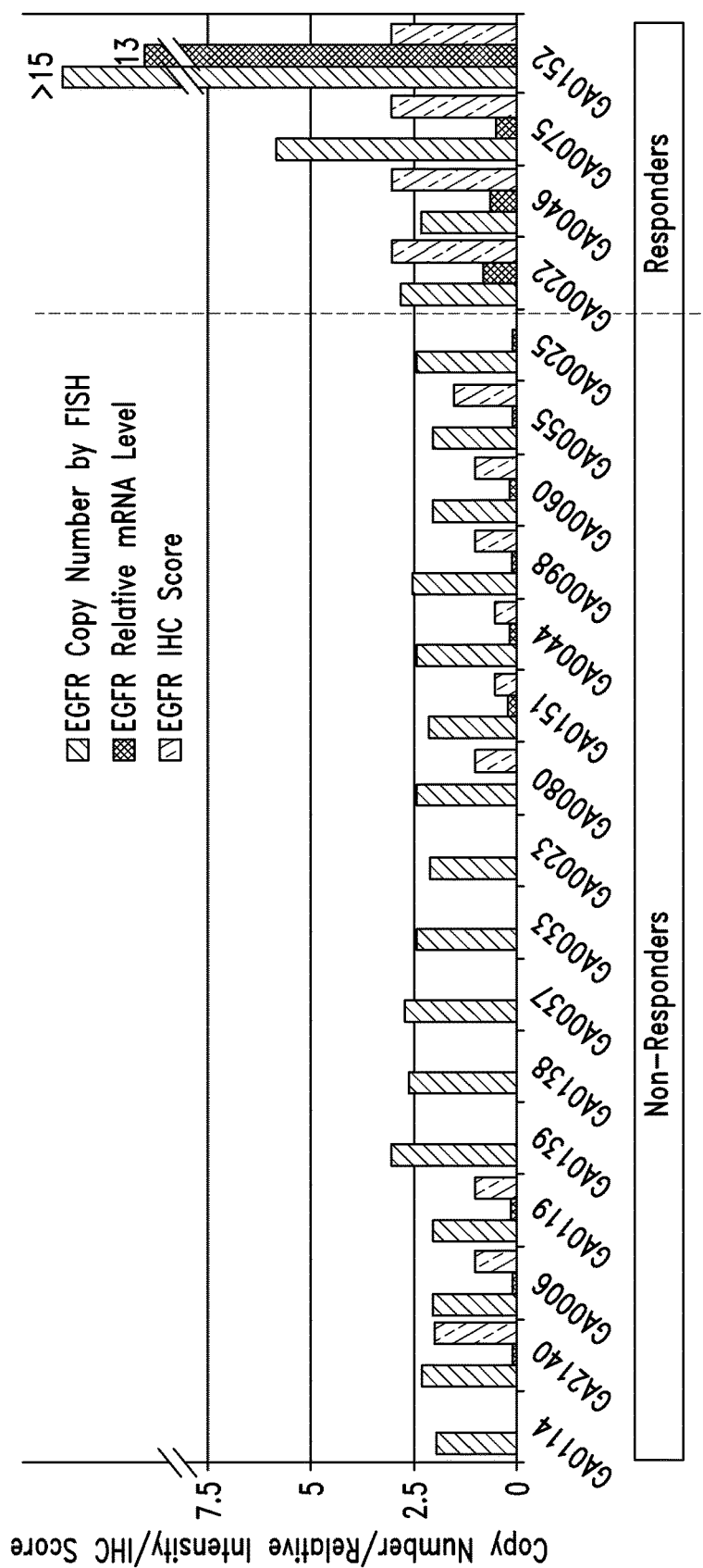

To further confirm the EGFR gene amplification, we further performed fluorescence in situ hybridization (FISH), a more accurate assay used to determine HER2 gene amplification for guiding anti-HER2 treatment for advanced GC in the clinical practice. At least 100 non-overlapping interphase nuclei were observed for the number of copies of EGFR. EGFR status was scored as the number of EGFR signals per nucleus. Our result demonstrated EGFR amplification in 2/4 (50%) responders with average copy number 5.8 (GA0075) and 0.15 (GA0152), respectively (FIG. 1C, Table 1). GA0152 was also with EGFR/CEP7 ratio 0.15. Thus, 2/4 (50%) responders could be predicted by EGFR amplification.

Next it was investigated whether EGFR signaling was indeed inactivated in these tumors by cetuximab by performing a single dose pharmacodynamic analysis. The tumor bearing animals were first treated with cetuximab and the tumors were harvested at time points of 6, 24 and 72 hours post treatment. As an example, GA0022 tumor tissues were analyzed post-treatment for pERK (a downstream effector of EGFR signaling) by immunochemistry analysis (IHC). The results clearly demonstrated the reduction of pERK in tumors (FIG. 1B), correlating to the observed antitumor activity in the same model.

The Factors Governing the Response to Cetuximab in CRC Seem to Contribute Significantly Less to the Response in GC-ADC.

In order to discover the predictive biomarker(s) for the observed response GC-ADC, this cohort of models was systemically profiled for expression and gene copy number, as well as genetic mutations, of some common oncogenes. Activating mutations, including those of KRAS, BRAF (V600E), c-MET, EGFR, AKT and PI3KC have been associated with resistance to cetuximab in CRC patients[15, 17-21]. Thus, these models were first analyzed by hot-spot mutation sequencing of these oncogenes. Interestingly, few of the tested models, regardless responders or non-responders, showed any mutations with exception of GA0139 containing G13D and GA044 containing 327-329 deletion in PIK3CA (Table 1). Therefore, the non-response of GC HuPrime® to cetuximab apparently cannot be simply attributed to these oncogene mutations.

Figure 3:
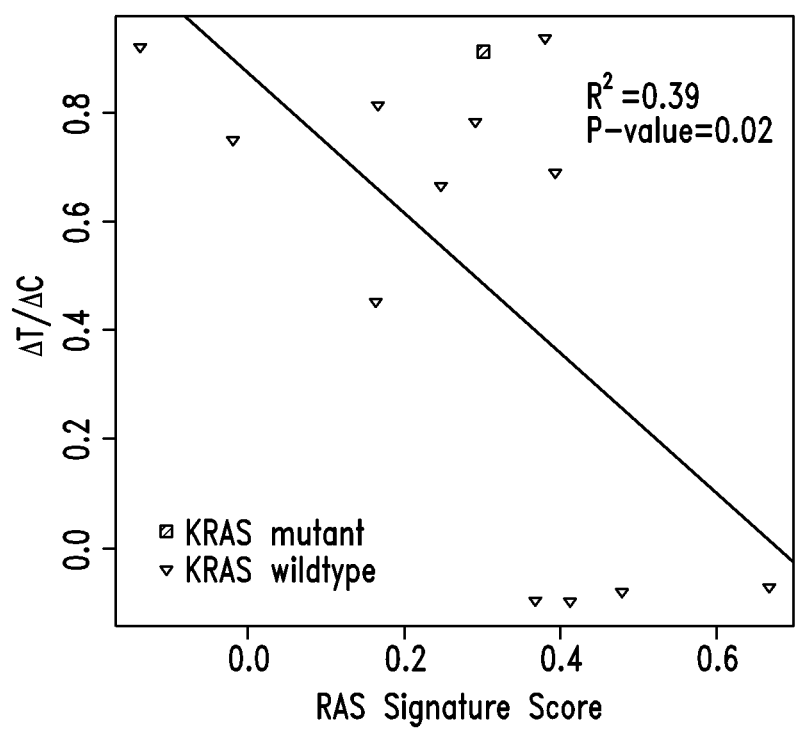
FIG. 3 Loboda RAS pathway signature scores were plotted against tumor size over time. The Loboda RAS pathway signature scores were found to have little correlation to the tumor response.

In a separate study earlier, it was observed that CRC HuPrime® response to cetuximab is dependent on RAS pathway signaling, or associated with the low Loboda-RAS pathway signature scores[17, 22]. It would therefore be interesting to know whether RAS signaling pathway or Loboda scores have similarly impacts on the GC HuPrime® response. To our surprise, Loboda RAS pathway signature scores were found to have little correlation to the tumor response (see FIG. 3), suggesting that the activation status of RAS pathway contribute significantly less to the response or resistance to cetuximab in GC-ADC than those seen in CRC.

EGFR Gene Amplification Seems to be an Oncogenic Driver in a Subset of GC-ADC HuPrime® that Respond to Cetuximab.

Figures 2A, 2B, 2C, 2D:
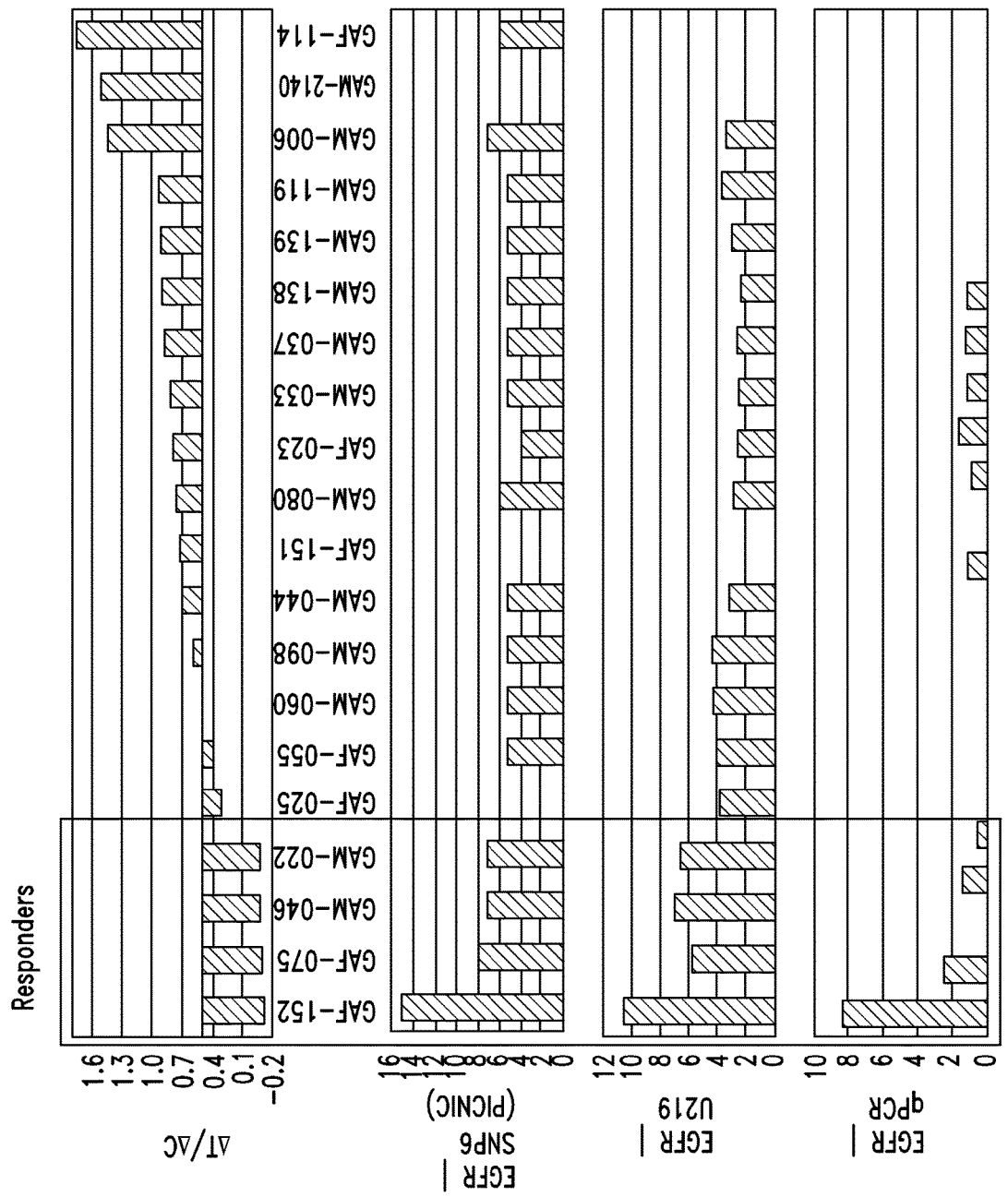
FIG. 2 The correlation of antitumor activities and EGFR gene amplification and over-expression. (Boxed items represent models with EGFR gene amplication). Panel A (FIG. 2A): Waterfall graph of GC-ADC tumor response to cetuximab; Panel B (FIG. 2B). EGFR gene copy number analysis of GC models using Affymetrix SNP6 chip analysis. Panel C (FIG. 2C). Relative mRNA levels as measured Affymetix GeneChip HG-U219. D EGFR mRNA expression as measured by pPCR.

However, on the other hand, Affymetix HG-U219 GeneChip analysis revealed that all of the 4 responders expressed high levels of EGFR (mRNA levels), and that all the 15 poor responders are associated with lower levels of expression (FIGS. 2A and 2C, Table 1). This observation seems plausible since the higher activity of EGFR via higher expression could drive the oncogenic transformation in these tumors and the inactivation by cetuximab could thus inhibit tumor growth.

Furthermore, it was investigated what genetic defects behind the higher EGFR expression by examining gene copy using Affymetrix SNP6 analysis (FIG. 2B). Interestingly, all the responders have the corresponding EGFR gene amplification (FIGS. 2A and 2B) (Table 1, Table 4) (P-value <0.00026 per Fisher's Exact Test). This near-perfect correlation suggested that EGFR gene amplification is likely the key oncogenic driver in the responders and a potential practical single biomarker for predicting response to cetuximab in GC-ADC. To further confirm the gene amplification, we also performed EGFR-fluorescence in situ hybridization, or FISH, a clinically practical assay, to assess EGFR gene amplification status of all these models. The FISH data indeed confirm the observations seen by SNP6. The GA152 FISH analysis as an example, clearly indicated EGFR amplification. The clinically accepted FISH procedure enables the development of companion diagnosis for cetuximab treatment in the clinic for cetuximab GC-ADC treatment.

TABLE 1A

Profiles of GC HuPrimer ® Model Panels

| model ID | T/C | EGFR SNP6 PICNIC | FGFR2 SNP6 | HER2 SNP6 | EGFR U219 intensity | EGFR (q-PCR) | EGFR (FISH) | CEP7 (FISH) | Ratio (EGFR/ CEP7) | EGFR Relative Intensity | Protein EGFR IHC Score Mutation |
|---|---|---|---|---|---|---|---|---|---|---|---|
| GA0114 | 1.62 | 6 | 15 | 5 | 2.9 | 5.1 | 1.9 | 1.9 | 0.96 | 0 | 0 |
| GA2140 | 1.32 | | | | NE | 3.8 | 2.3 | 2.2 | 1.04 | 0.1 | 2 |
| GA0119 | 0.93 | 5 | 3 | 5 | 3.6 | 2.1 | 2 | 2 | 1.03 | 0.14 | 1 |
| GA0139 | 0.91 | 5 | 5 | 15 | 2.9 | 4.8 | 3 | 2.7 | 1.09 | 0 | 0 |
| GA0138 | 0.9 | 5 | 5 | 5 | 2.3 | 2.7 | 2.6 | 2 | 1.29 | 0 | 0 |
| GA0037 | 0.88 | 5 | 5 | 6 | 2.5 | 3.7 | 2.7 | 2.3 | 1.16 | 0 | 0 |
| GA0033 | 0.81 | 5 | 15 | 4 | 2.4 | 3.9 | 2.4 | 2 | 1.21 | 0.02 | 0 |
| GA0023 | 0.78 | 4 | 4 | 5 | 2.5 | 1.9 | 2.1 | 2.5 | 0.83 | 0.02 | 0 |
| GA0080 | 0.75 | 6 | 6 | 4 | 2.8 | 3.7 | 2.4 | 2.1 | 1.16 | 0.02 | 1 |
| GA0151 | 0.7 | | | | 4 | 1.4 | 2.1 | 2.2 | 0.93 | 0.2 | 1 |
| GA0044 | 0.69 | 5 | 6 | 4 | 3.1 | 2.1 | 2.4 | 2.3 | 1.03 | 0.13 | 1 |
| GA0098 | 0.55 | 5 | 4 | 5 | 4.2 | 3.7 | 2.5 | 2.1 | 1.2 | 0.07 | 1 |
| GA0060 | 0.45 | 5 | 4 | 15 | 4.2 | 3.1 | 2 | 2.2 | 0.91 | 0.13 | 1 |
| GA0025 | 0.31 | | | | 3.8 | 2.1 | 2.3 | 2.3 | 1.05 | 0.1 | 0 |
| Responders Shown below | | | | | | | | | | | |
| GA0022 | −0.071 | 7 | 5 | 4 | 6.5 | 5.4 | 2.8 | 2 | 1.39 | 0.81 | 3 |
| GA046 | −0.072 | 7 | 4 | 3 | 6.9 | 4.3 | 2.3 | 2.3 | 1.03 | 0.62 | 3 |
| GA0075 | −0.098 | 8 | 4 | 5 | 5.8 | 4.6 | 5.8 | 2 | 1.12 | 0.5 | 3 |
| GA0152 | −0.121 | 15 | 3 | 5 | 10.5 | 1040.9 | >15 | | >15 | 13 | 3 |
| P value (non- vs. responders | 0.002 | 0.002 | | | 0.003 | 0.008 | 0.029 | | 0.099 | 0.002 | 0.002 |

TABLE 1B

Profiles of GC HuPrimer ® Model Panels

| model ID | EGFR Exon 18;19;20;21 | k-RAS Exon 2;3;4 | BRAF Exon 15 | c-MET Exon 14;16;17; 18;19;21 | PIK3CA Exon1;9;20 |
|---|---|---|---|---|---|
| GA0114 | WT | WT | WT | WT | WT |
| GA2140 | | | | | |
| GA0119 | WT | WT | WT | WT | WT |
| GA0139 | WT | G13D | WT | WT | WT |
| GA0138 | WT | WT | WT | WT | WT |
| GA0037 | WT | WT | WT | WT | WT |
| GA0033 | WT | WT | WT | WT | WT |
| GA0023 | WT | WT | WT | WT | WT |
| GA0080 | WT | WT | WT | WT | WT |
| GA0151 | WT | WT | WT | WT | WT |
| GA0044 | WT | WT | WT | WT | deletion 327-329 |
| GA0098 | WT | WT | WT | WT | G545Y |
| GA0060 | WT | WT | WT | WT | WT |
| GA0025 | WT | WT | WT | WT | WT |
| Responders Shown below | | | | | |
| GA0022 | WT | WT | WT | WT | WT |
| GA046 | WT | WT | WT | WT | WT |
| GA0075 | WT | WT | WT | WT | WT |
| GA0152 | WT | WT | WT | WT | WT |

NE: not evaluable

TABLE 2

GC Patient Diagnosis and Pathology, and The Corresponding Model Pathology Confirmation

| ID | Gender | Original hospital pathology report |
|---|---|---|
| GA0114 | F | Gastric adenocarcinoma. |
| GA2140 | M | Moderately to poorly differentiated adenocarcinoma of gastric body to antrum with necrosis, tumor mass: 12 × 11 cm. The tumor invades through gastric wall. Regional LN: NO. 1 LN (0/6), NO. 2 LN (0/1), NO. 3 LN (0/6), NO. 5 LN (0/2), NO. 6 LN (0/2), NO. 7, 8, 9 LN (0/5), NO. 4d LN (0/4). IHC results: CD44 (+), cMet (+), EGFR (+), HER2 (1+), Ki-67 (+>75%), MMP7 (+), P170 (+), P27 (+25~50%), P53 (+<25%), TOPOII (+50~75%). |
| GA0119 | M | Adenocarcinoma of gastric cardia with mucinous adenocarcinoma and some signet-ring cell carcinoma, ulcerative type, poorly differentiated, tumor mass: 6.5 cm × 7 cm × 2 cm, invaded serosa and nerve plexus. Malignant cells adjacent to inferior stump. Regional LN: LN of lesser curvature (6/6), left gastric LN (5/6), inferior pyloric LN (1/1). |
| GA0139 | M | Adenocarcinoma of gastric cardia with papillary adenocarcinoma, ulcerative type, moderately differentiated, tumor mass: 6.5 cm × 7 cm × 1 cm, invaded adipose tissue external serosa. No malignant cells adjacent to both stump. Regional LN: LN of lesser curvature (0/11), paraesophageal LN (0/4). |
| GA0138 | M | Adenocarcinoma of stomach, invasive, ulcerative type, poorly differentiated, tumor mass: 11 cm × 9 cm × 3 cm, invaded deep muscular layer, no visible malignant cells adjacent to both stump. Regional LN: LN of lesser curvature (1/5). |

TABLE 2-continued

GC Patient Diagnosis and Pathology, and The Corresponding Model Pathology Confirmation

| ID | Gender | Original hospital pathology report |
|---|---|---|
| GA0037 | M | Adenocarcinoma of gastric cardia, ulcerative type, poorly differentiated, tumor mass: 4 cm × 4 cm × 2.5 cm, invaded serosa. No visible malignant cells adjacent to both stump. Regional LN: LN of lesser curvature (0/9). |
| GA0033 | M | Adenocarcinoma of gastric cardia, ulcerative type, poorly differentiated, tumor mass: 9 cm × 6 cm × 1.5 cm, invaded serosa, and accompanied with necrosis and a few lymphocytes deposition. No visible malignant cells adjacent to both stump. Regional LN: cardial LN (0/5), left gastric LN (0/7). |
| GA0023 | F | Adenocarcinoma, ulcerative type, poorly differentiated. |
| GA0080 | M | 1. Adenocarcinoma of gastric cardia, invasive type, moderately-poorly differentiated, tumor mass: 8 cm × 6 cm × 1.5 cm, invaded serosa. No visible malignant cells adjacent to both stump. Regional LN: Regional LN: cardial LN (1/5), left gastric LN (2/2). 2. Hepatitis, type B |
| GA0044 | M | Metastatic adenocarcinoma derived from liver, moderately-poorly differentiated. The patient had been done gastric cancer surgery 2 years ago. |
| GA0025 | F | Signet-ring cell carcinoma of gastric greater curvature, parts are mucinous adenocarcinoma, protruded type, tumor mass: 3.5 cm × 3.5 cm × 2 cm, invaded through gastric wall. Regional LN: LN surround celiac trunk (1/1). IHC results: HER-1 (−), HER-2 (−), p53 (−), p170 (−), Ki-67 (+25~50%), VEGF (+), Top-IIα (+<25%), p16 (−). |

Responders Shown below

| ID | Gender | Original hospital pathology report |
|---|---|---|
| GA0022 | M | Adenocarcinoma of gastic cardia, ulcerative type, moderately-poorly differentiated, tumor mass: 5 cm × 4 cm × 2.5 cm, invaded through gastric wall to serosa. No visible malignant cells adjacent to both stump. Regional LN: left gastric LN (5/9), LN of inferior parapulmonary vein (0/6). |
| GA0046 | M | Adenocarcinoma derived from juncture of stomach and esophagus in lesser gastric curvature, protruded ulcerative type, poorly differentiated, tumor mass: 6 cm × 5 cm × 1.5 cm. Malignant cells invade through gastric wall and esophagus. Regional LN: LN of lesser curvature (3/14). IHC results: HER-1 (+), HER-2 (−), P53 (+25~50%), P170 (−), Ki-67 (+25~50, VEGF (++), Top-IIα (+ about 10%). p16 (−). |
| GA0075 | F | Adenocarcinoma of cardia and fundus of stomach, infiltrating ulcerative type, moderately-poorly differentiated, tumor mass: 6.5 cm × 5 cm × 1.5 cm, invaded serosa. No malignant cells adjacent to both stump. Regional LN: LN of lesser curvature (1/6), cardial LN (0/4), LN of greater curvature (0/4), LN of para-inferior pulmonary vein (0/3). |
| GAF152 | F | Poorly differentiated adenocarcinoma (P0, P5). |

TABLE 3

Clinicopathological parameters of GC patients and pathology confirmation of corresponding PDX models.

| ID | Sex | Tumor Size (cm) | Depth of Wall Invasion | Lymph Node Metastasis | Distant Metastasis | TNM stages | Histology (patients and PDX) | Differentiation |
|---|---|---|---|---|---|---|---|---|
| GA0006 | M | >5.0 | T4a | N1 | M0 | IIIa | adenocarcinoma | moderately-poorly |
| GA0022 | M | ≤5.0 | T4a | N2 | M0 | IIIb | adenocarcinoma | moderately-poorly |
| GA0023 | F | ≤5.0 | T4a | N2 | M0 | IIIb | adenocarcinoma | poorly |
| GA0025 | F | ≤5.0 | T4a | N1 | M0 | IIIa | signet-ring cell carcinoma | poorly |
| GA0033 | M | >5.0 | T4a | N0 | M0 | IIb | adenocarcinoma | poorly |
| GA0037 | M | ≤5.0 | T4a | N0 | M0 | IIb | adenocarcinoma | poorly |
| GA0044 | M | lesion from liver | n/a | n/a | M1 | IV | adenocarcinoma | moderately-poorly |
| GA0046 | M | >5.0 | T4a | N2 | M0 | IIIb | adenocarcinoma | poorly |
| GA0055 | F | ≤5.0 | T4a | N3b | M0 | IIIc | adenocarcinoma | moderately |
| GA0060 | M | ≤5.0 | T4a | N3a | M0 | IIIc | adenocarcinoma | moderately-poorly |
| GA0075 | F | >5.0 | T4a | N1 | M0 | IIIa | adenocarcinoma | moderately-poorly |
| GA0080 | M | >5.0 | T4a | N2 | M0 | IIIb | adenocarcinoma | moderately-poorly |
| GA0098 | M | ≤5.0 | T4a | N0 | M0 | IIb | adenocarcinoma | moderately |
| GA0114 | F | >5.0 | T4a | N1 | M0 | IIIa | adenocarcinoma | moderately-poorly |
| GAG119 | M | >5.0 | T4a | N3b | M0 | IIIc | adenocarcinoma | poorly |
| GA0138 | M | >5.0 | T2 | N1 | M0 | IIa | adenocarcinoma | poorly |
| GA0139 | M | >5.0 | T4a | N0 | M0 | IIb | adenocarcinoma | well |
| GA0151 | F | >5.0 | T4a | N1 | M0 | IIIa | adenocarcinoma | moderately-poorly |
| GA0152 | F | >5.0 | T4a | N0 | M0 | IIb | adenocarcinoma | poorly |
| GA2140 | M | >5.0 | T4a | N0 | M0 | IIb | adenocarcinoma | moderately-poorly |

* Stage of GC was classified according to 7$^{th}$ edition tumor-node-metastasis (TNM) classification recommended by the International Union Against Cancer.

TABLE 4

EGFR copy number determined by different methods.

| model ID | EGFR SNP6 PICNIC | EGFR qPCR | EGFR FISH |
|---|---|---|---|
| GA0114 | 6 | | N/A |
| GA2140 | | | N/A |
| GA0119 | 5 | | 0.99 |
| GA0139 | 5 | 1.06 | |
| GA0138 | 5 | 0.96 | |
| GA0037 | 5 | 1.50 | |
| GA0033 | 5 | +0.64 | |
| GA0023 | 4 | 0.00 | |
| GA0080 | 6 | 0.94 | |
| GA0151 | | N/A | |
| GA0044 | 5 | N/A | |
| GA0098 | 5 | N/A | |
| GA0060 | 5 | N/A | + |
| GA0025 | N/A | 0.32 | |
| Responders Shown below | | | |
| GA0022 | 7 | 1.21 | |
| GA046 | 7 | N/A | |
| GA0075 | 8 | 2.29 | |
| GA0152 | 15 | 8.22 | |

TABLE 5

Panel of primers used for mutation analyses.

| Mutation | | Primers |
|---|---|---|
| EGFR | | |
| Exon 18 | Forward | 5'-CATGGTGAGGGCTGAGGTGA-3' (SEQ ID NO: 1) |
| | Reverse | 5'-CCCCACCAGACCATGAGAGG-3' (SEQ ID NO: 2) |
| Exon 19 | Forward | 5'-GTGCATCGCTGGTAACATCCA-3' (SEQ ID NO: 3) |
| | Reverse | 5'-GGAGATGAGCAGGGTCTAGAGCA-3' (SEQ ID NO: 4) |
| Exon 20 | Forward | 5'-CGCATTCATGCGTCTTCACC-3' (SEQ ID NO: 5) |
| | Reverse | 5'-CTATCCCAGGAGCGCAGACC-3' (SEQ ID NO: 6) |
| Exon 21 | Forward | 5'-TGGCATGAACATGACCCTGAA-3' (SEQ ID NO: 7) |
| | Reverse | 5'-CAGCCTGGTCCCTGGTGTC-3' (SEQ ID NO: 8) |
| KRAS | | |
| Exon 2 | Forward | 5'-TTATGTGTGACATGTTCTAAT-3' (SEQ ID NO: 9) |
| | Reverse | 5'-AGAATGGTCCTGCACCAGTAA-3' (SEQ ID NO: 10) |
| Exon 3 | Forward | 5'-TCAAGTCCTTTGCCCATTTT-3' (SEQ ID NO: 11) |
| | Reverse | 5'-TGCATGGCATTAGCAAAGAC-3' (SEQ ID NO: 12) |
| Exon 4 | Forward | 5'-TTGTGGACAGGTTTTGAAAGA-3' (SEQ ID NO: 13) |
| | Reverse | 5'-AGAAGCAATGCCCTCTCAAG-3' (SEQ ID NO: 14) |
| BRAF | | |
| Exon 15 | Forward | 5'-CTCTTCATAATGCTTGCTC-3' (SEQ ID NO: 15) |
| | Reverse | 5'-GTGAATACTGGGAACTATG-3' (SEQ ID NO: 16) |
| c-MET | | |
| Exon 14 | Forward | 5'-TGGGCACTGGGTCAAAGTCTC-3' (SEQ ID NO: 17) |
| | Reverse | 5'-AACAATGTCACAACCCACTGAGGTA-3' (SEQ ID NO: 18) |
| Exon 16 | Forward | 5'-ATTAAATGTTACGCAGTGCTAAC-3' (SEQ ID NO: 19) |
| | Reverse | 5'-GGTTGCAAACCACAAAAGTAT-3' (SEQ ID NO: 20) |
| Exon 17 | Forward | 5'-GTATTCACTGTTCCATAATGAAGT-3' (SEQ ID NO: 21) |
| | Reverse | 5'-GATGGCTGGCTTACAGCTAGTT-3' (SEQ ID NO: 22) |
| Exon 18 | Forward | 5'-AACAGTAGATGCTTAGTTTATGCT-3' (SEQ ID NO: 23) |
| | Reverse | 5'-AACAGATTCCTCCTTGTCACTT-3' (SEQ ID NO: 24) |
| Exon 19 | Forward | 5'-TTCTATTTCAGCCACGGGTAAT-3' (SEQ ID NO: 25) |
| | Reverse | 5'-ATGAAAGTAAAAGAGGAGAAACTC-3' (SEQ ID NO: 26) |
| Exon 21 | Forward | 5'-CACCCTAAAGCCGAAATGCG-3' (SEQ ID NO: 27) |
| | Reverse | 5'-CAAGGAGCAAAGAATATCGATGGC-3' (SEQ ID NO: 28) |
| PI3KCA | | |
| Exon 1 | Forward | 5'-CTCCACGACCATCATCAGG-3' (SEQ ID NO: 29) |
| | Reverse | 5'-GATTACGAAGGTATTGGTTTAGACAG-3' (SEQ ID NO: 30) |
| Exon 9 | Forward | 5'-GATTGGTTCTTTCCTGTCTCTG-3' (SEQ ID NO: 31) |
| | Reverse | 5'-CCACAAATATCAATTTACAACCATTG-3' (SEQ ID NO: 32) |
| Exon 20 | Forward | 5'-TGGGGTAAAGGGAATCAAAAG-3' (SEQ ID NO: 33) |
| | Reverse | 5'-CCTATGCAATCGGTCTTTGC-3' (SEQ ID NO: 34) |

All Responders Display Higher EGFR mRNA Expression Level.

On the other hand, transcriptome profiling using Affymetrix HG-U219 GeneChip, revealed that all of the four responders expressed higher levels of EGFR mRNA expression than all 16 non-responders did (P=0.003) (Table 1). EGFR gene expression was further quantified by q-RT-PCR (quantitative reverse transcription-PCR) against housekeeping gene GAPDH. Among the samples tested, 4 samples exhibited high EGFR mRNA levels (relative intensity ≥0.5, arbitrarily defined) were all responders, in contrast to the remaining models showing medium to low EGFR mRNA levels (relative intensity ≤0.1) (Table 1, FIG. 1C). The difference is significant (P=0.002). In particular, the highest value is from GA0152, with 10.5 by GeneChip analysis and 13 by q-RT-PCR, which can be attributed to the EGFR amplification mentioned above.

All Responders Display Higher EGFR Immunohistochemistry Score.

Then we performed EGFR immunohistochemistry (IHC), a clinically practical assay to determine HER2 expression for anti-HER2 treatment for GC. IHC demonstrated positive EGFR immunostaining in 12/20 (60%) models. Among them, 6/12 had staining intensity score of 1+, 3/12 of 2+, and 3/12 of 3+. All responders were found EGFR IHC 31, while the non-responders displayed lower EGFR IHC score 0 (P 5 0.002) (Table 1, FIG. 1C). The typical EGFR strong immunostaining (GA0152 and GA0075) is showed in FIG. 1B. These results demonstrated that the EGFR high expression (in both mRNA and protein level) is correlated to the response to cetuximab. Mutation of associated oncogenes is rare. Genetic mutations of some common oncogenes associated with EGFR pathway, e.g. KRAS, BRAF (V600E), c-MET, EGFR, AKT and PI3KC have also been investigated in these models by hot-spot mutation sequencing. Interestingly, few of the tested models, regardless responders or nonresponders, showed any aberrations with exception of GA0139 containing G13D KRAS mutation, GA0044 containing 327-329 deletion in PIK3CA, and GA0098 containing G545Y PIK3CA mutation (Table 1). Therefore, the non-response of GC xenografts to cetuximab apparently cannot be simply attributed to these oncogene mutations.

Discussion

This study clearly demonstrated that a subset of GC-ADC HuPrime® models with EGFR gene amplification and over expression responded to cetuximab (4/4). Consistent with this, 4 out of 4 EGFR amplified patients in EXTRA phase II trial were responders to the combination treatment of cetuximab and cisplatin/capecitabine (NCT00477711)[16], supporting the assumed predicative power of PDX models and our hypothesis of EGFR-predictive biomarker for cetuximab GC-ADC treatment. This assumption can also be further confirmed by retrospectively examining recently completed phase III trial in gastro-esophageal carcinoma, EXPAND, when the data becomes available. FISH for EGFR gene amplification can routinely be performed in the clinic setting, thus enabling this to be used as a companion diagnostic. Therefore, such a prospective trial can readily be implemented. The ultimate approval would offer one more targeted therapy option for GC-ADC patients, in addition to trastuzumab (Herceptin®) for patients with HER2 gene amplification[3].

The heavy dependency on EGFR gene amplification seen in GC HuPrime® response to cetuximab was however not observed in NSCLC (Yang et al., in submission) and CRC[17] HuPrime®, suggesting drastic difference among different cancer types. Very interestingly, this EGFR dependency in GC-ADC somehow mirrors the Her2 dependency for trastuzumab response in GC-ADC. This similarity provides a clear feasible development path for a companion diagnostic for cetuximab treatment of GC, just as the companion diagnostic for trastuzumab.

Figure 4A:
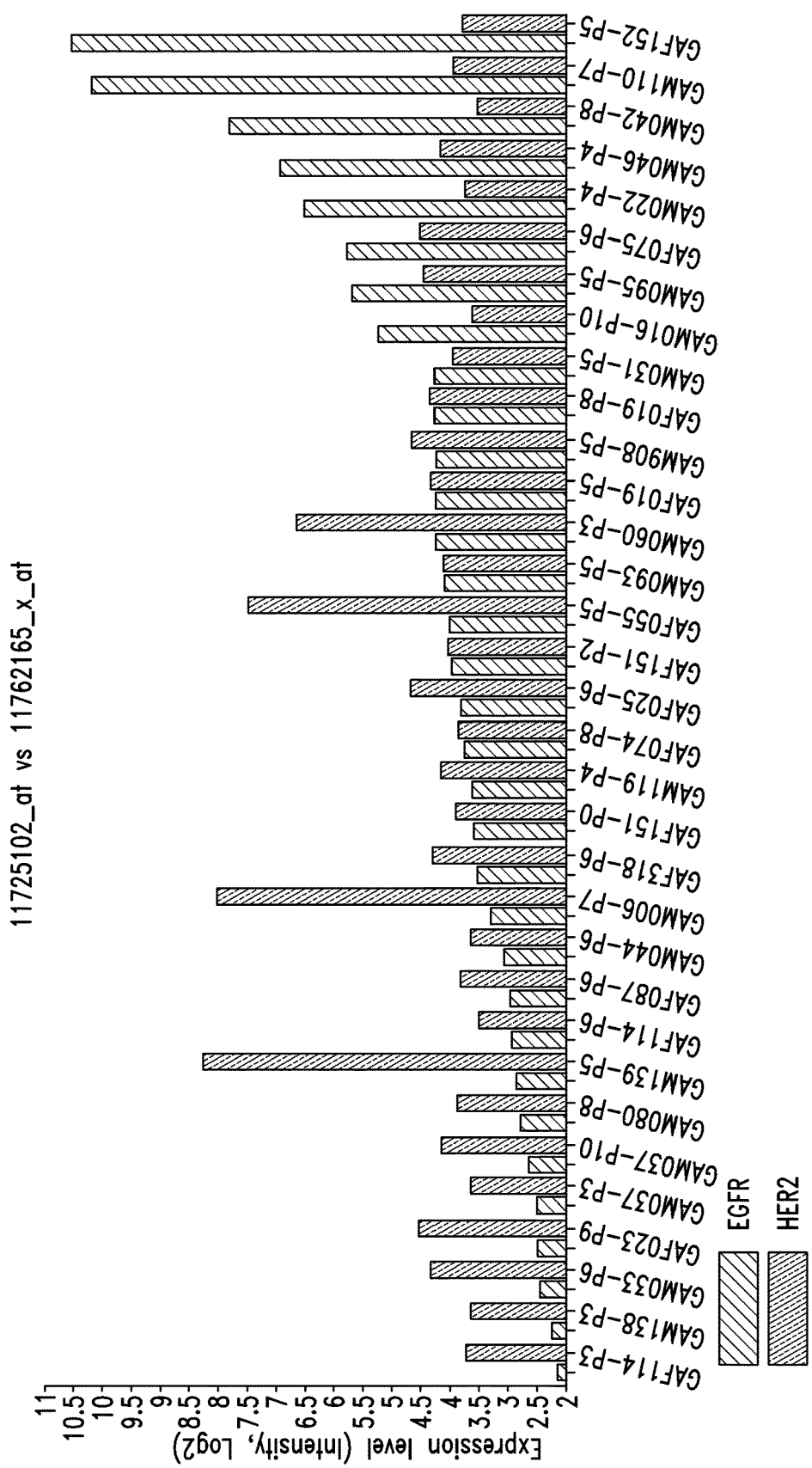
FIG. 4 GC-ADC HuPrime® models with EGFR over expression/gene amplification do not have HER2 overexpression/gene amplification. Panel A: EGFR and HER2 expression levels; Panel B: EGFR and HER2 gene copy number.
Figure 4B:
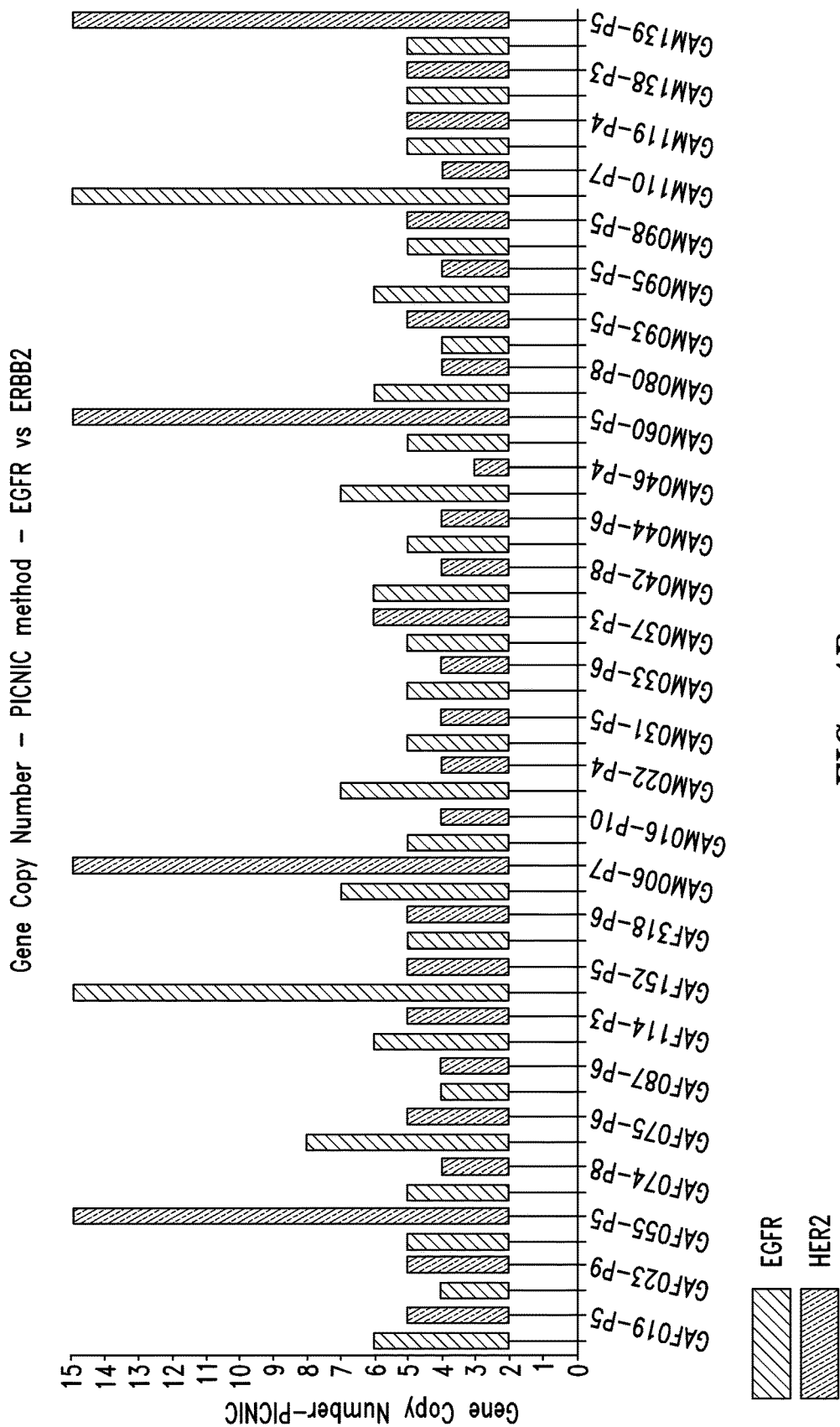
Figure 5:
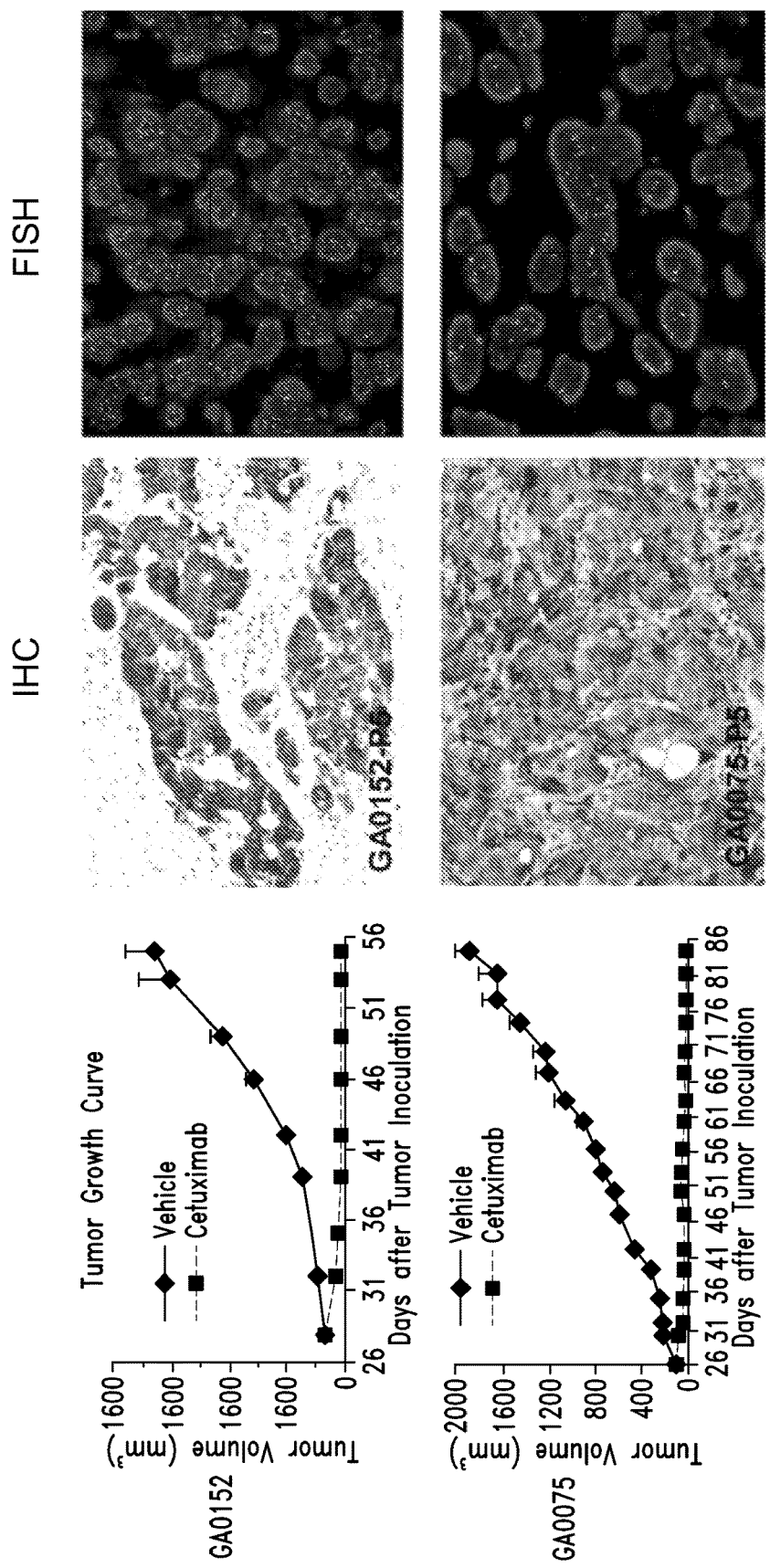
FIG. 5 The representative images of responders and non-responders. The responders GA0152 and GA0075 display IHC score 3+, and gene amplification (GA0075, CN=5.8; GA0152, CN>15), while non-responders GA0119 and GA0139 are with IHC low expression and no gene amplification. Left: Representative tumor growth curves of responders and non-responders. Middle: IHC analysis of tumor models; Right: Dual-color FISH assay in gastric carcinoma.
Figure 5:
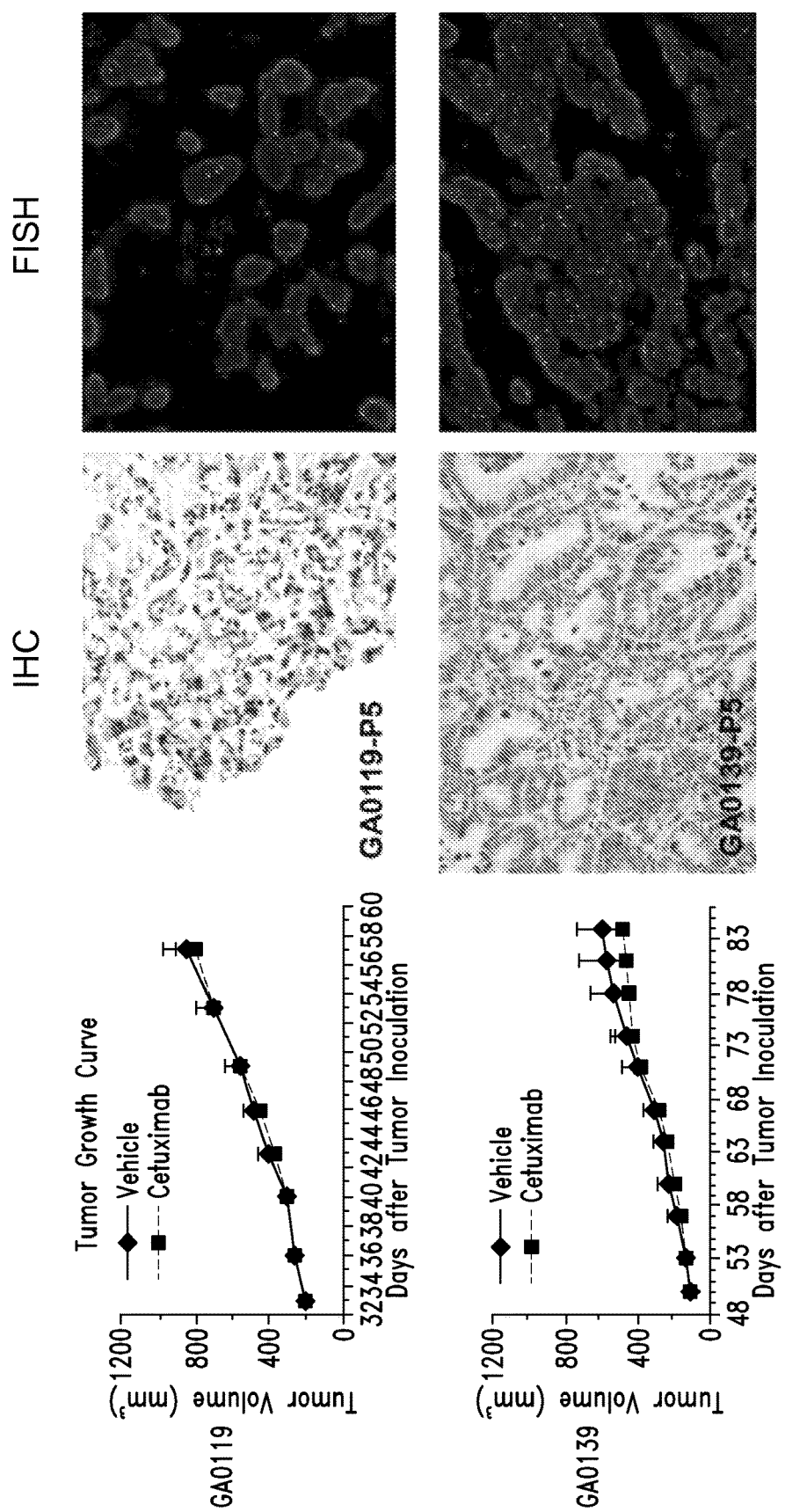

Another interesting observation is that the models with EGFR over expression (also gene amplifications) do not have HER2 over-expression (or gene amplification), and vice versa, i.e. no over-expression (gene amplification) of both of these genes was observed in a single model (see FIGS. 4A and 4B). This observation indicates that amplification/overexpression of both genes does not drive oncogenesis. Thus, it is reasonable that there would be no reason to use the combination of cetuximab and trastuzumab for GC patient treatment.

Our data point to a positive correlation between cetuximab response in GC and the EGFR high expression at both mRNA and protein level, as well as EGFR gene amplification. This correlation is exemplified by GA0152 that has the highest EGFR mRNA expression, IHC score and gene amplification. The data seem to suggest the higher activity of EGFR via higher expression drives the oncogenic transformation in these tumors, and therefore its inactivation by cetuximab thus inhibits tumor growth. Overexpression of EGFR could be attributes to the gene amplification in two cases.

Our data also demonstrated the EGFR high expression in both mRNA and protein level is correlated to the response. However, since the mRNA expression of EGFR genes is not routinely assayed in the clinical samples, and IHC can be of controversy due to biological and technical factors, we recommend that the combination of FISH and IHC tests are suitable for predicting cetuximab efficacy as routine clinical practice, similar to the clinical practice of anti-HER2 treatment.

In summary, our study suggests that a GC subtype with high EGFR mRNA expression and IHC score may benefit from cetuximab treatment, and the EGFR gene amplification by FISH can also accurately predict the responders with positive predictive value around 50%. These markers can be helpful for guiding future a potentially successful clinical trial and eventually as a patient stratification guide for clinical treatment.

REFERENCES

1. Kamangar F, Dores G M, Anderson W F. Patterns of cancer incidence, mortality, and prevalence across five continents: defining priorities to reduce cancer disparities in different geographic regions of the world. J Clin Oncol. 2006 May 10; 24(14):2137-50.
2. Kelley J R, Duggan J M. Gastric cancer epidemiology and risk factors. J Clin Epidemiol. 2003 January; 56(1):1-9.
3. Bang Y J, Van Cutsem E, Feyereislova A, Chung H C, Shen L, Sawaki A, et al. Trastuzumab in combination with chemotherapy versus chemotherapy alone for treatment of HER2-positive advanced gastric or gastro-oesophageal junction cancer (ToGA): a phase 3, open-label, randomised controlled trial. Lancet. 2010 Aug. 28; 376 (9742):687-97.
4. Ciardiello F, Tortora G. EGFR antagonists in cancer treatment. N Engl J Med. 2008 Mar. 13; 358(11):1160-74.
5. Bonner J A, Harari P M, Giralt J, Cohen R B, Jones C U, Sur R K, et al. Radiotherapy plus cetuximab for locoregionally advanced head and neck cancer: 5-year survival data from a phase 3 randomised trial, and relation between cetuximab-induced rash and survival. Lancet Oncol. January; 11(1):21-8.
6. Pinto C, Di Fabio F, Barone C, Siena S, Falcone A, Cascinu S, et al. Phase II study of cetuximab in combination with cisplatin and docetaxel in patients with untreated advanced gastric or gastro-oesophageal junction adenocarcinoma (DOCETUX study). Br J Cancer. 2009 Oct. 20; 101(8):1261-8.
7. Pinto C, Di Fabio F, Siena S, Cascinu S, Rojas Llimpe F L, Ceccarelli C, et al. Phase II study of cetuximab in combination with FOLFIRI in patients with untreated advanced gastric or gastroesophageal junction adenocarcinoma (FOLCETUX study) Ann Oncol. 2007 March; 18(3):510-7.
8. Lordick F, Luber B, Lorenzen S, Hegewisch-Becker S, Folprecht G, Woll E, et al. Cetuximab plus oxaliplatin/leucovorin/5-fluorouracil in first-line metastatic gastric cancer: a phase II study of the Arbeitsgemeinschaft Internistische Onkologie (AIO). Br J Cancer. 2010 Feb. 2; 102(3):500-5.
9. Ding L, Ellis M J, Li S, Larson D E, Chen K, Wallis J W, et al. Genome remodelling in a basal-like breast cancer metastasis and xenograft. Nature. 2010 Apr. 15; 464 (7291):999-1005.
10. Marangoni E, Vincent-Salomon A, Auger N, Degeorges A, Assayag F, de Cremoux P, et al. A new model of patient tumor-derived breast cancer xenografts for preclinical assays. Clin Cancer Res. 2007 Jul. 1; 13(13):3989-98.
11. Nemati F, Sastre-Garau X, Laurent C, Couturier J, Mariani P, Desjardins L, et al. Establishment and characterization of a panel of human uveal melanoma xenografts derived from primary and/or metastatic tumors. Clin Cancer Res. 2010 Apr. 15; 16(8):2352-62.
12. Nemati F, Daniel C, Arvelo F, Legrier M E, Froget B, Livartowski A, et al. Clinical relevance of human cancer xenografts as a tool for preclinical assessment: example of in-vivo evaluation of topotecan-based chemotherapy in a panel of human small-cell lung cancer xenografts. Anticancer Drugs. 2010 January; 21(1):25-32.
13. Fichtner I, Rolff J, Soong R, Hoffmann J, Hammer S, Sommer A, et al. Establishment of patient-derived non-small cell lung cancer xenografts as models for the identification of predictive biomarkers. Clin Cancer Res. 2008 Oct. 15; 14(20):6456-68.
14. Hennessey P T, Ochs M F, Mydlarz W W, Hsueh W, Cope L, Yu W, et al. Promoter methylation in head and neck squamous cell carcinoma cell lines is significantly different than methylation in primary tumors and xenografts. PLoS One. 2011; 6(5):e20584.
15. Yang M, Xiaoming Song, Jianyun Deng, Jie Cai, Taiping Chen, Jean-Pierre Wery, Yiyou Chen and Qixiang Li. Overcoming drug resistance with tailored treatment regimen in patient derived xenografts from naïve Asian NSCLC patients resistant to EGFR inhibitors. 2012; Submitted.
16. Zhang X, Jianming Xu, Lin Shen, Lin Yang, Jun Liang, Nong Xu, Yuxian Bai6, Jiejun Wang. A Multicenter Prospective Phase II study of Cetuximab with Cisplatin/Capecitabine for untreated patients with Advanced Gastric or Esophago-gastric Adenocarcinoma (EXTRA study). 2012.
17. Chen D, Petra Ross-Macdonald, Sheng Guo, Jie Cai, Rolf Ryseck, Craig Fairchild, Heshani de Silva, Jian Cao, Aiqing He, Xiaoming Song, Mengmeng Yang, Jianyun Deng, Taiping Chenl, Jean-Pierre Weryl, Yiyou Chenl and Qixiang Li. Cetuximab response in CRC patient-derived xenografts is predicted by RAS pathway activation rather than KRAS mutation status. 2012.
18. Lievre A, Bachet J B, Le Corre D, Boige V, Landi B, Emile J F, et al. KRAS mutation status is predictive of response to cetuximab therapy in colorectal cancer. Cancer Res. 2006 Apr. 15; 66(8):3992-5.
19. De Roock W, Claes B, Bernasconi D, De Schutter J, Biesmans B, Fountzilas G, et al. Effects of KRAS, BRAF, NRAS, and PIK3CA mutations on the efficacy of cetuximab plus chemotherapy in chemotherapy-refractory metastatic colorectal cancer: a retrospective consortium analysis. Lancet Oncol. 2010 August; 11(8):753-62.
20. De Roock W, De Vriendt V, Normanno N, Ciardiello F, Tejpar S. KRAS, BRAF, PIK3CA, and PTEN mutations: implications for targeted therapies in metastatic colorectal cancer. Lancet Oncol. 2011 June; 12(6):594-603.
21. Di Nicolantonio F, Martini M, Molinari F, Sartore-Bianchi A, Arena S, Saletti P, et al. Wild-type BRAF is required for response to panitumumab or cetuximab in metastatic colorectal cancer. J Clin Oncol. 2008 Dec. 10; 26(35):5705-12.
22. Loboda A, Nebozhyn M, Klinghoffer R, Frazier J, Chastain M, Arthur W, et al. A gene expression signature of RAS pathway dependence predicts response to PI3K and RAS pathway inhibitors and expands the population of RAS pathway activated tumors. BMC Med Genomics. 2010; 3:26.
23. Jemal et al. C A. Caner J. Clin. 61, 69-90 (2011)
24. Han et al., Phase II study and biomarker analysis of cetuximab combined with modified FOLFOX6 in advanced gastric cancer *Br. J. Cancer* 100, 298-304 (2009)
25. Kim et al. A prospective phase II study of cetuximab in combination with XELOX (capecitabine and oxaliplatin) in patients with metastatic and/or recurrent advanced gastric cancer. Invest. New Drugs 29, 366-373 (2011)
26. Lordick et al. Capecitabine and cisplatin with or without cetuimab for patients with previously untreated advanced gastric cancer (EXPAND): a randomised, open-label phase 3 trial. *Lancet Oncol.* 14, 490-499 (2013)
27. Luber et al. Biomarker analysis of cetuximab pus oxaliplatin/leucovorin/5-fluorouracil in first-line metastatic gastric and oesophago-gastric junction cancer: results from a phase II trial of the Arbeitsgemeinschaft Internistische Onkologie (AIO) *BMC Cancer* 11, 509 (2011)
28. Shia et al., Epidermal growth factor receptor expression and gene amplification in colorectal carcinoma: an immunohistochemical and chromogenic in situ hbridization study. *Mod. Pathol.*

What is claimed is:

1. A method for treating gastric neoplasia consisting of administering to a patient in need of such treatment an effective amount of cetuximab, wherein the patient has been determined to have an EGFR gene copy number biomarker in a tumor tissue obtained from the patient before the treatment, and wherein the patient is expected to be more responsive to the treatment compared to patients not having the EGFR gene copy number biomarker, wherein the EGFR gene copy number biomarker is selected from the group consisting of (1) an EGFR gene copy number of at least 7 as determined by Affymetrix genome-wide human SNP6.0 array and PICNIC (Predicting Integral Copy Numbers In Cancer) algorithm, (2) an EGFR gene copy number of at least 4 as determined by realtime quantitative PCR, and (3) an EGFR gene copy number of at least 2.8 as determined by fluorescence in situ hybridization (FISH).

2. The method of claim 1, wherein the gastric neoplasia is gastric adenocarcinoma.

3. A method for treating gastric neoplasia consisting of administering to a patient in need of such treatment an effective amount of cetuximab, wherein the patient has been determined to have an EGFR overexpression biomarker in a tumor tissue obtained from the patient before the treatment, wherein the patient is expected to be more responsive to the treatment compared to patients not having the EGFR overexpression biomarker, wherein the EGFR overexpression biomarker is selected from the group consisting of (1) an EGFR mRNA level of at least 5.0 as measured by Affymetrix GeneChip HG-U219, (2) a relative EGFR gene expression level of at least 0.5 as measured by quantitative RT-PCR, and (3) an EGFR protein level of at least 3 as measured by immunohistorchemical (IHC) analysis.

4. The method of claim 1, wherein the EGFR gene copy number is determined by a hybridization assay.

5. The method of claim 3, wherein the patient has been determined not to have a HER2 biomarker.

6. The method of claim 1, wherein the patient has been determined not to have a HER2 biomarker.

7. The method of claim 1, wherein the tumor tissue is a tissue extract sample or a biopsy sample.

8. The method of claim 3, wherein the tumor tissue is a tissue extract sample or a biopsy sample.

* * * * *

UNITED STATES PATENT AND TRADEMARK OFFICE
CERTIFICATE OF CORRECTION

PATENT NO. : 10,442,862 B2
APPLICATION NO. : 14/775117
DATED : October 15, 2019
INVENTOR(S) : Yang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 224 days.

Signed and Sealed this
Second Day of June, 2020

Andrei Iancu
*Director of the United States Patent and Trademark Office*

SEQUENCE LISTING

<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: EGFR EXON 18 forward primer

<400> SEQUENCE: 1

```
catggtgagg gctgaggtga                                            20

<210> SEQ ID NO 2
<211> LENGTH: 20
<212> TYPE: DNA
<213> ORGANISM: Artificial Sequence
<220> FEATURE:
<223> OTHER INFORMATION: EGFR EXON 18 reverse primer

<400> SEQUENCE: 2
ccccaccaga ccatgagagg                                            20

<210> SEQ ID NO 3
<211> LENGTH: 21
<212> TYPE: DNA
<213> ORGANISM: Artificial Sequence
<220> FEATURE:
<223> OTHER INFORMATION: EGFR EXON 19 forward primer

<400> SEQUENCE: 3
gtgcatcgct ggtaacatcc a                                          21

<210> SEQ ID NO 4
<211> LENGTH: 23
<212> TYPE: DNA
<213> ORGANISM: Artificial Sequence
<220> FEATURE:
<223> OTHER INFORMATION: EGFR EXON 19 reverse primer

<400> SEQUENCE: 4
ggagatgagc agggtctaga gca                                        23

<210> SEQ ID NO 5
<211> LENGTH: 20
<212> TYPE: DNA
<213> ORGANISM: Artificial Sequence
<220> FEATURE:
<223> OTHER INFORMATION: EGFR EXON 20 forward primer

<400> SEQUENCE: 5
cgcattcatg cgtcttcacc                                            20

<210> SEQ ID NO 6
<211> LENGTH: 20
<212> TYPE: DNA
<213> ORGANISM: Artificial Sequence
<220> FEATURE:
<223> OTHER INFORMATION: EGFR EXON 20 reverse primer

<400> SEQUENCE: 6
ctatcccagg agcgcagacc                                            20

<210> SEQ ID NO 7
<211> LENGTH: 21
<212> TYPE: DNA
<213> ORGANISM: Artificial Sequence
<220> FEATURE:
<223> OTHER INFORMATION: EGFR EXON 21 forward primer

<400> SEQUENCE: 7
tggcatgaac atgaccctga a                                          21

<210> SEQ ID NO 8
<211> LENGTH: 19
<212> TYPE: DNA
<213> ORGANISM: Artificial Sequence
```

```
<220> FEATURE:
<223> OTHER INFORMATION: EGFR EXON 21 reverse primer

<400> SEQUENCE: 8
cagcctggtc cctggtgtc                                                    19

<210> SEQ ID NO 9
<211> LENGTH: 21
<212> TYPE: DNA
<213> ORGANISM: Artificial Sequence
<220> FEATURE:
<223> OTHER INFORMATION: KRAS EXON 2 forward primer

<400> SEQUENCE: 9
ttatgtgtga catgttctaa t                                                 21

<210> SEQ ID NO 10
<211> LENGTH: 21
<212> TYPE: DNA
<213> ORGANISM: Artificial Sequence
<220> FEATURE:
<223> OTHER INFORMATION: KRAS EXON 2 reverse primer

<400> SEQUENCE: 10
agaatggtcc tgcaccagta a                                                 21

<210> SEQ ID NO 11
<211> LENGTH: 20
<212> TYPE: DNA
<213> ORGANISM: Artificial Sequence
<220> FEATURE:
<223> OTHER INFORMATION: KRAS EXON 3 forward primer

<400> SEQUENCE: 11
tcaagtcctt tgcccatttt                                                   20

<210> SEQ ID NO 12
<211> LENGTH: 20
<212> TYPE: DNA
<213> ORGANISM: Artificial Sequence
<220> FEATURE:
<223> OTHER INFORMATION: KRAS EXON 3 reverse primer

<400> SEQUENCE: 12
tgcatggcat tagcaaagac                                                   20

<210> SEQ ID NO 13
<211> LENGTH: 21
<212> TYPE: DNA
<213> ORGANISM: Artificial Sequence
<220> FEATURE:
<223> OTHER INFORMATION: KRAS EXON 4 forward primer

<400> SEQUENCE: 13
ttgtggacag gttttgaaag a                                                 21

<210> SEQ ID NO 14
<211> LENGTH: 20
<212> TYPE: DNA
<213> ORGANISM: Artificial Sequence
<220> FEATURE:
<223> OTHER INFORMATION: KRAS EXON 4 reverse primer

<400> SEQUENCE: 14
agaagcaatg ccctctcaag                                                   20
```

```
<210> SEQ ID NO 15
<211> LENGTH: 19
<212> TYPE: DNA
<213> ORGANISM: Artificial Sequence
<220> FEATURE:
<223> OTHER INFORMATION: BRAF Exon 15 forward primer

<400> SEQUENCE: 15
ctcttcataa tgcttgctc                                                  19

<210> SEQ ID NO 16
<211> LENGTH: 19
<212> TYPE: DNA
<213> ORGANISM: Artificial Sequence
<220> FEATURE:
<223> OTHER INFORMATION: BRAF Exon 15 reverse primer

<400> SEQUENCE: 16
gtgaatactg ggaactatg                                                  19

<210> SEQ ID NO 17
<211> LENGTH: 21
<212> TYPE: DNA
<213> ORGANISM: Artificial Sequence
<220> FEATURE:
<223> OTHER INFORMATION: c-MET Exon 14 forward primer

<400> SEQUENCE: 17
tgggcactgg gtcaaagtct c                                               21

<210> SEQ ID NO 18
<211> LENGTH: 25
<212> TYPE: DNA
<213> ORGANISM: Artificial Sequence
<220> FEATURE:
<223> OTHER INFORMATION: c-MET Exon 14 reverse primer

<400> SEQUENCE: 18
aacaatgtca caacccactg aggta                                           25

<210> SEQ ID NO 19
<211> LENGTH: 23
<212> TYPE: DNA
<213> ORGANISM: Artificial Sequence
<220> FEATURE:
<223> OTHER INFORMATION: c-MET Exon 16 forward primer

<400> SEQUENCE: 19
attaaatgtt acgcagtgct aac                                             23

<210> SEQ ID NO 20
<211> LENGTH: 21
<212> TYPE: DNA
<213> ORGANISM: Artificial Sequence
<220> FEATURE:
<223> OTHER INFORMATION: c-MET Exon 16 reverse primer

<400> SEQUENCE: 20
ggttgcaaac cacaaaagta t                                               21

<210> SEQ ID NO 21
<211> LENGTH: 24
<212> TYPE: DNA
<213> ORGANISM: Artificial Sequence
<220> FEATURE:
<223> OTHER INFORMATION: c-MET Exon 17 forward primer
```

```
<400> SEQUENCE: 21
gtattcactg ttccataatg aagt                                          24

<210> SEQ ID NO 22
<211> LENGTH: 22
<212> TYPE: DNA
<213> ORGANISM: Artificial Sequence
<220> FEATURE:
<223> OTHER INFORMATION: c-MET Exon 17 reverse primer

<400> SEQUENCE: 22
gatggctggc ttacagctag tt                                            22

<210> SEQ ID NO 23
<211> LENGTH: 24
<212> TYPE: DNA
<213> ORGANISM: Artificial Sequence
<220> FEATURE:
<223> OTHER INFORMATION: c-MET Exon 18 forward primer

<400> SEQUENCE: 23
aacagtagat gcttagttta tgct                                          24

<210> SEQ ID NO 24
<211> LENGTH: 22
<212> TYPE: DNA
<213> ORGANISM: Artificial Sequence
<220> FEATURE:
<223> OTHER INFORMATION: c-MET Exon 18 reverse primer

<400> SEQUENCE: 24
aacagattcc tccttgtcac tt                                            22

<210> SEQ ID NO 25
<211> LENGTH: 22
<212> TYPE: DNA
<213> ORGANISM: Artificial Sequence
<220> FEATURE:
<223> OTHER INFORMATION: c-MET Exon 19 forward primer

<400> SEQUENCE: 25
ttctatttca gccacgggta at                                            22

<210> SEQ ID NO 26
<211> LENGTH: 24
<212> TYPE: DNA
<213> ORGANISM: Artificial Sequence
<220> FEATURE:
<223> OTHER INFORMATION: c-MET Exon 19 reverse primer

<400> SEQUENCE: 26
atgaaagtaa aagaggagaa actc                                          24

<210> SEQ ID NO 27
<211> LENGTH: 20
<212> TYPE: DNA
<213> ORGANISM: Artificial Sequence
<220> FEATURE:
<223> OTHER INFORMATION: c-MET Exon 21 forward primer

<400> SEQUENCE: 27
caccctaaag ccgaaatgcg                                               20

<210> SEQ ID NO 28
```

```
<211> LENGTH: 24
<212> TYPE: DNA
<213> ORGANISM: Artificial Sequence
<220> FEATURE:
<223> OTHER INFORMATION: c-MET Exon 21 reverse primer

<400> SEQUENCE: 28
caaggagcaa agaatatcga tggc                                          24

<210> SEQ ID NO 29
<211> LENGTH: 19
<212> TYPE: DNA
<213> ORGANISM: Artificial Sequence
<220> FEATURE:
<223> OTHER INFORMATION: PI3KCA Exon 1 forward primer

<400> SEQUENCE: 29
ctccacgacc atcatcagg                                                19

<210> SEQ ID NO 30
<211> LENGTH: 26
<212> TYPE: DNA
<213> ORGANISM: Artificial Sequence
<220> FEATURE:
<223> OTHER INFORMATION: PI3KCA Exon 1 reverse primer

<400> SEQUENCE: 30
gattacgaag gtattggttt agacag                                        26

<210> SEQ ID NO 31
<211> LENGTH: 22
<212> TYPE: DNA
<213> ORGANISM: Artificial Sequence
<220> FEATURE:
<223> OTHER INFORMATION: PI3KCA Exon 9 forward primer

<400> SEQUENCE: 31
gattggttct ttcctgtctc tg                                            22

<210> SEQ ID NO 32
<211> LENGTH: 26
<212> TYPE: DNA
<213> ORGANISM: Artificial Sequence
<220> FEATURE:
<223> OTHER INFORMATION: PI3KCA Exon 9 reverse primer

<400> SEQUENCE: 32
ccacaaatat caatttacaa ccattg                                        26

<210> SEQ ID NO 33
<211> LENGTH: 21
<212> TYPE: DNA
<213> ORGANISM: Artificial Sequence
<220> FEATURE:
<223> OTHER INFORMATION: PI3KCA Exon 20 forward primer

<400> SEQUENCE: 33
tggggtaaag ggaatcaaaa g                                             21

<210> SEQ ID NO 34
<211> LENGTH: 20
<212> TYPE: DNA
<213> ORGANISM: Artificial Sequence
<220> FEATURE:
<223> OTHER INFORMATION: PI3KCA Exon 20 reverse primer

<400> SEQUENCE: 34
```

```
cctatgcaat cggtctttgc                                                        20
```